(12) United States Patent
Lim

(10) Patent No.: US 8,669,067 B2
(45) Date of Patent: Mar. 11, 2014

(54) CANCER BIOMARKER AND THE USE THEREOF

(75) Inventor: Yoon Pin Lim, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/386,357

(22) PCT Filed: Jul. 23, 2010

(86) PCT No.: PCT/SG2010/000280
§ 371 (c)(1), (2), (4) Date: Jan. 20, 2012

(87) PCT Pub. No.: WO2011/010969
PCT Pub. Date: Jan. 27, 2011

(65) Prior Publication Data
US 2012/0190050 A1    Jul. 26, 2012

(30) Foreign Application Priority Data

Jul. 23, 2009    (SG) ............................... 200904976-8

(51) Int. Cl.
*G01N 33/574*    (2006.01)

(52) U.S. Cl.
USPC .......................................... 435/7.23; 436/64

(58) Field of Classification Search
None
See application file for complete search history.

(56) References Cited

FOREIGN PATENT DOCUMENTS

| WO | WO-2004/048550 A2 | 6/2004 |
| WO | WO-2007/047796 A2 | 4/2007 |
| WO | WO-2007/100183 A1 | 9/2007 |
| WO | WO-2008/085828 A2 | 7/2008 |
| WO | WO-2010/096154 A2 | 8/2010 |
| WO | WO-2011/010969 A1 | 1/2011 |

OTHER PUBLICATIONS

Oleesky et al (Clin Endocrinol 25:623-32, 1986, abstract.*
Hicke et al, J Nucle Med 147: 668-678, 2006.*
Definition of complement system, Medical Dictionary, 2013.*
Extended European Search Report mailed Nov. 26, 2012 for EP 10802526.3.
Kim et al., Value of serial carcinoembryonic antigen levels in patients with resectable adenocarcinoma of the esophagus and stomach. Cancer. Jan. 15, 1995;75(2):451-6.
Crepaldi-Filho et al., Levels of carcinoembryonic antigen and CA 19-9 in the sera and peritoneal washing of patients undergoing surgical treatment for gastric carcinoma. Arq Gastroenterol. Jul.-Sep. 2008;45(3):219-24.
International Search Report with Written Opinion mailed Oct. 8, 2010 in connection with PCT/SG2010/000280.
International Preliminary Report on Patentability mailed Dec. 2, 2011 in connection with PCT/SG2010/000280.
Chong et al., Upregulation of plasma C9 protein in gastric cancer patients. Proteomics. Sep. 2010;10(18):3210-21. Epub Jul. 21, 2010.
Ikebukuro et al., Selection and characterization of DNA aptamers against VEGF165 with aptamer blotting method and its application. Nucleic Acids Symp Ser (Oxf). Nov. 2007;(51):399-400.
Shangguan et al., Aptamers evolved from live cells as effective molecular probes for cancer study. Proc Natl Acad Sci U S A. Aug. 8, 2006;103(32):11838-43. Epub Jul. 27, 2006.
Shangguan et al., Cell-specific aptamer probes for membrane protein elucidation in cancer cells. J Proteome Res. May 2008;7(5):2133-9. Epub Mar. 26, 2008.
Te Velde et al., Acute phase reactants and complement components as indicators of recurrence in human cervical cancer. Eur J Cancer. Jun. 1979;15(6):893-9.

* cited by examiner

*Primary Examiner* — Lei Yao
(74) *Attorney, Agent, or Firm* — Wolf, Greenfield & Sacks, P.C.

(57) ABSTRACT

Gastric cancer is one of the leading causes of cancer-related death worldwide. To date no specific marker is available for gastric cancer screening. The expression profile of 37 proteins was identified to be consistently different between the plasma of normal and gastric cancer subjects. The expression of complement component C9 protein was validated to be significantly higher in the plasma of gastric cancer compared to normal subjects. This was independent of the gastritis and *H. pylori* status of the patients. We also observed a statistically significant difference (p<0.04) in the expression level of C9 between patients with intestinal and diffuse types of cancer. Two independent blind test studies showed a high sensitivity and specificity to detect gastric cancer. The C9 protein is a biomarker for screening gastric cancer.

10 Claims, 12 Drawing Sheets

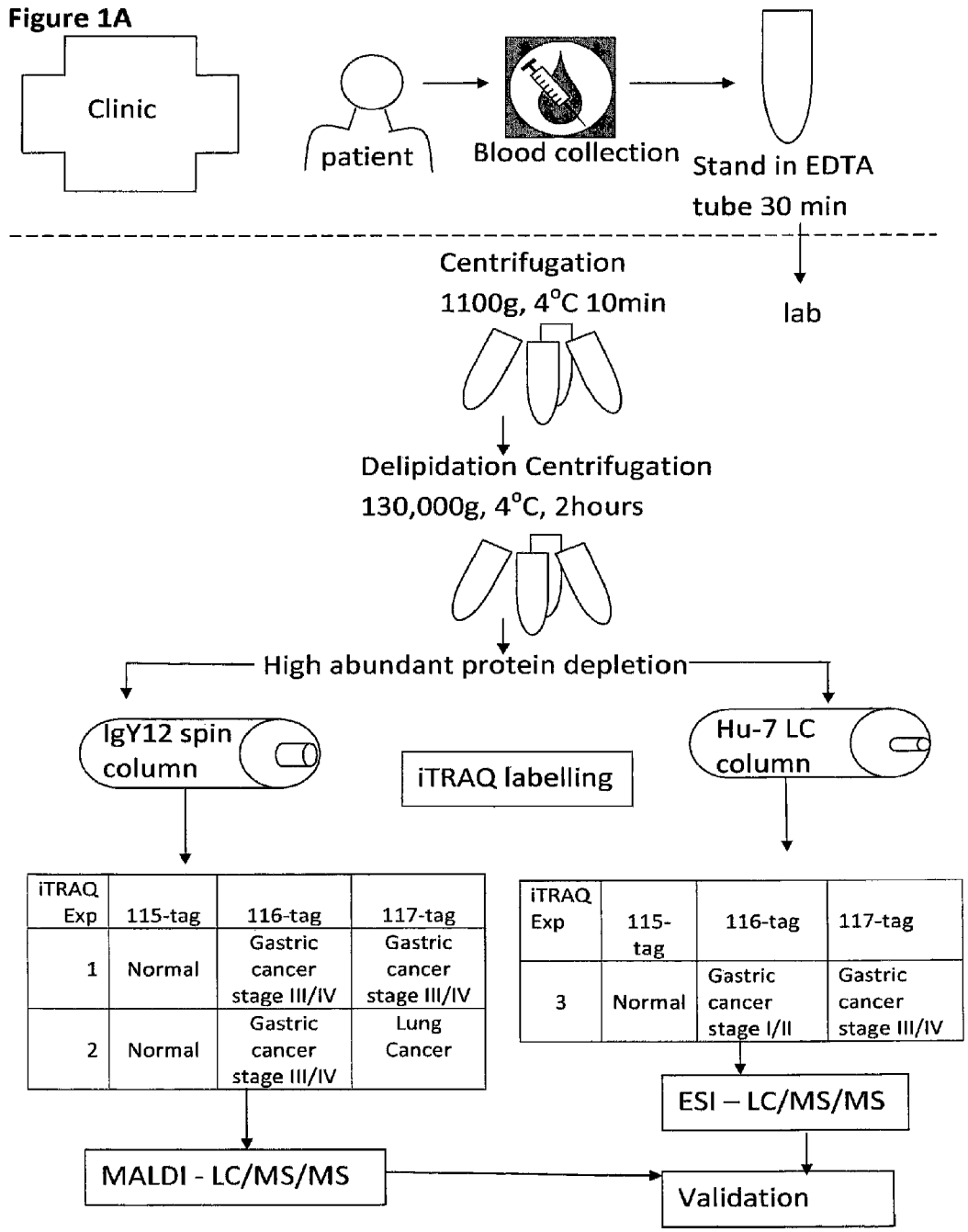

(C) Late Gastric Cancer Samples (Stage III and IV)

(D) Baseline Lung Cancer Samples

CANCER BIOMARKER AND THE USE THEREOF

CROSS-REFERENCE TO RELATED APPLICATION

This application is a U.S. National Stage application based on International Application No. PCT/SG2010/000280, filed on 23 Jul. 2010, which claims benefit of, and priority from, Singapore patent application No. 200904976-8, filed on 23 Jul. 2009 the contents of which are hereby incorporated by reference.

FIELD OF THE INVENTION

The present invention relates to diagnostic or prognostic biomarker or biomarkers for screening or detection of gastric cancer.

BACKGROUND ART

Gastric cancer or stomach cancer refers to tumors that develop in the lower part of the esophagus, in the stomach or in the uppermost part of the small intestine. Gastric cancer is a leading cause of cancer-related death worldwide in which almost one million new cases are being diagnosed yearly (Lam, K. W., Lo, S. C., Proteomics Clin. Appl. 2008, 2, 219-228). The global 5-year survival rate is around 20% except for Japan with close to 60% (Kamangar F, et al. J Clin Oncol 2006; 24:2137-50). Interesting discrepancies between the Western and Eastern populations had been reported in terms of the frequency of early detection and prognosis of the disease, probably resulting from the differences in gastric cancer epidemiology, staging systems and treatments (Davis, P. A., Japanese journal of clinical oncology 2000, 30, 463-464). Early detection is believed to be a key pillar in the management of gastric cancer. Population screening by endoscopy introduced in Japan and other Eastern countries leads to almost 70% of gastric cancer being diagnosed in early stage compared to merely 15% in Western countries where screening remains elusive (Cunningham and Chua, The New England journal of medicine 2007, 357, 1863-1865). However the cost effectiveness of population screening in other countries apart from Japan and Korea remains questionable. Screening of high risk subjects may be a viable alternative (Yeoh, K. G., Journal of gastroenterology and hepatology 2007, 22, 970-972. Leung, W. K., et al., The lancet oncology 2008, 9, 279-287). However, there is currently no specific biomarker available for gastric cancer screening and diagnosis in the clinic and the commonly used markers such as CA19-9, fetoprotein antigen, pepsinogen I/II, carcinoembryonic antigen (CEA) etc are insensitive (Lam and Lo 2008). Clearly there is a need to find better molecular markers.

Conventional tumor markers such as CA19-9, CA72-4 and CEA are not adequately sensitive and/or specific for gastric cancer detection. A recent review summarized the tumor marker sensitivity in gastric cancer detection including CEA at 16% to 63%, CA19-9 at 20% to 56% and CA72-4 at 18% to 51% (Ebert, M. P., Rocken, C., European journal of gastroenterology & hepatology 2006, 18, 847-853). The specificity of these markers was not defined. M2-pyruvate kinase (M2-PK), described as tumor-associated metabolic marker, had also been evaluated for gastric cancer detection, with the sensitivity and specificity ranged from 57% to 67% and 89% to 95% respectively (Kumar, Y., et al. European journal of gastroenterology & hepatology 2007, 19, 265-276.;] Hardt, P. D., et al. Anticancer research 2000, 20, 4965-4968.; Cerwenka, H., et al., Anticancer research 1999, 19, 849-851. In general, 2 conclusions could be derived from these reports: i) the current tumor markers candidates have a sensitivity of less than 67% for gastric cancer and ii) most of them are not specific for any cancer type.

Classification of gastric cancer is often based on the Lauren classification. This is probably the most successful and widely used today (Vauhkonen, M., et al. Best practice & research 2006, 20, 651-674). Based on Lauren classification, gastric cancer can be classified into two main cancer pathogeneses:—(i) intestinal (IGCA) and (ii) diffuse (DGCA) subtypes. These two subtypes show significant differences in epidemiologic and prognostic features, which excite clinicians and oncologists to pursue further understanding of the basis for classification (Kountouras, J., et al. Hepato-gastroenterology 2005, 52, 1305-1312). The proportion of intestinal type (IGCA) accounts for approximately 50%, that of the diffuse type (DGCA) 35% and the remainder 15% is characterized as "unclassified" or mixed type cancer. The intestinal type (IGCA) is characterized by cohesive neoplastic cells forming gland like tubular structures, whereas in diffuse type (DGCA) cell cohesion is absent, so that individual cells infiltrate and thicken the stomach wall without forming a discrete mass. This difference in microscopic growth pattern is also reflected in the different macroscopic appearance of the two histological subtypes. Whereas for intestinal type (IGCA) the macroscopic margins correspond approximately to the microscopic spread, the diffuse type (DGCA) as a poorly differentiated cancer can extend submucosally far beyond its macroscopic borders. This difference in tumor spread of the two types of Lauren-classification is of clinical importance in decision-making about appropriate treatment options. The intestinal type (IGCA) predominate in high-risk areas, occur more often in distal stomach, and is often preceded by a prolonged precancerous phase, whereas diffuse type (DGCA) tumors prevail among young patients and women and the contribution of hereditary factors to their causation is higher. Classification of gastric cancer based on the Lauren classification requires invasive sampling methods.

The advancement in analytical tools and mass spectrometry platforms has spurred the quest of biomarker discovery. Proteomics approaches in unearthing biomarkers have shown successes in breast, prostate, lung, ovarian cancer and to a smaller extent in gastric cancer in which potential candidates have been identified from tumour tissue (He, Q. Y., et al., Proteomics 2004, 4, 3276-3287) and cell lines (Takikawa, M., et al., Oncology reports 2006, 16, 705-711). For example, one study employed two-dimensional gel electrophoresis (2-DE) approach to profile disease-specific protein expression from gastric juice (Lee, K., et al., Proteomics 2004, 4, 3343-3352). Another 2-DE approach further identified 14 differentially expressed proteins in gastric cancer versus normal tissues (Ryu, J. W., et al., Journal of Korean medical science 2003, 18, 505-509). Although studies on tumour and gastric juice had provided great insights on the disease, biomarker discovery based on these approaches engage invasive sampling methods and are not ideal from a clinical point of view.

Some groups have mined blood samples for biomarkers using a ProteinChip system, which is based on the surface enhanced laser desorption/ionization (SELDI) approach (Liang, Y., et al., Experimental and molecular pathology 2006, 81, 176-180); (Ebert, M. P., et al., Journal of proteome research 2004, 3, 1261-1266); (Poon, T. C., et al., Gastroenterology 2006, 130, 1858-1864). Although differences were found in the peptide mass fingerprint, this information is incomplete without knowing the identities of the protein. Although, a recent paper had successfully developed the methodology to identify SELDI profile peaks using Protein-Chip coupled with a tandem mass spectrometer (Peng, J., et al. *Proteomics* 2009, 9, 492-498) one should be cautioned that reproducing the serum profiling using SELDI could be difficult due to various intrinsic or extrinsic factors. On the other hand, one study employed conventional 2-DE gel coupled with mass spectrometric analysis and revealed that the upregulation of cathepsin B in the sera of gastric cancer patients can be used as a prognosis marker but not for early diagnostic (Ebert, M. P., et al., *Proteomics* 2005, 5, 1693-1704). However, sensitivity remains an issue with 2-DE approach and detection of low abundance proteins remains challenging. This problem is further amplified by the fact that proteins in the blood have a wide protein dynamic range spanning over 10 orders of magnitude.

The typical role of C9 is in the innate immune system, which is one of the host's defense systems against foreign bodies. C9 is a part of the terminal pathway in the complement system and together with C5b, C6, C7 and C8 is required for the assembly of membrane attack complex leading to cell lysis.

SUMMARY OF THE INVENTION

The present invention seeks to provide novel methods for detecting or screening for gastric cancer to ameliorate some of the difficulties with, and complement the current methods of detection or screening of gastric cancer. The invention further seeks to provide kits to detect or screen for gastric cancer.

We have discovered that Complement protein C9 and/or other proteins are over expressed in body fluid taken from patients with gastric cancer when compared with the expression of the proteins in body fluid taken from normal patents having no signs of gastric cancer.

Accordingly one aspect of the present invention provides a method of detecting the presence of a cancer in an individual suspected or at risk of having cancer comprising the steps of (a) measuring the concentration of Compliment component C9 protein in a suitable fluid sample obtained from the individual, and (b) comparing the concentration measured in step (a) with a standard value ranges for the concentration of Compliment component C9 protein for healthy individuals, wherein when the concentration of Compliment component C9 protein obtained from the individual is increased as compared to the standard value range for the concentration of Compliment component C9 protein of healthy individuals it is indicative of the possible presence of a cancer.

Another aspect of the invention provides a method of detecting the presence of a gastric cancer in an individual suspected or at risk of having gastric cancer comprising the steps of (a) measuring the concentration of Compliment component C9 protein in a suitable fluid sample obtained from the individual, and (b) comparing the concentration measured in step (a) with a standard value ranges for the concentration of Compliment component C9 protein for healthy individuals, wherein when the concentration of Compliment component C9 protein obtained from the individual is increased as compared to the standard value range for the concentration of Compliment component C9 protein of healthy individuals it is indicative for the possible presence of a gastric cancer.

Another aspect of the invention provides a kit to detect a potential gastric cancer in a suitable fluid sample comprising an antibody capable of binding selectively a Compliment component C9 protein and reagents for detection of a complex formed between the antibody and a complement component C9 protein.

Another aspect of the invention provides use of a concentration of Compliment component C9 protein in a suitable fluid sample as a biomarker for gastric cancer.

Another aspect of the invention provides an isolated antibody capable of binding selectively a Compliment component C9 protein for use in detecting gastric cancer by measuring a concentration of Compliment component C9 protein in a suitable fluid sample.

Yet another aspect of the invention provides an aptamer capable of binding selectively a Compliment component C9 protein for use in detecting gastric cancer by measuring a concentration of Compliment component C9 protein in a suitable fluid sample.

DETAILED DESCRIPTION

Figure 1B:
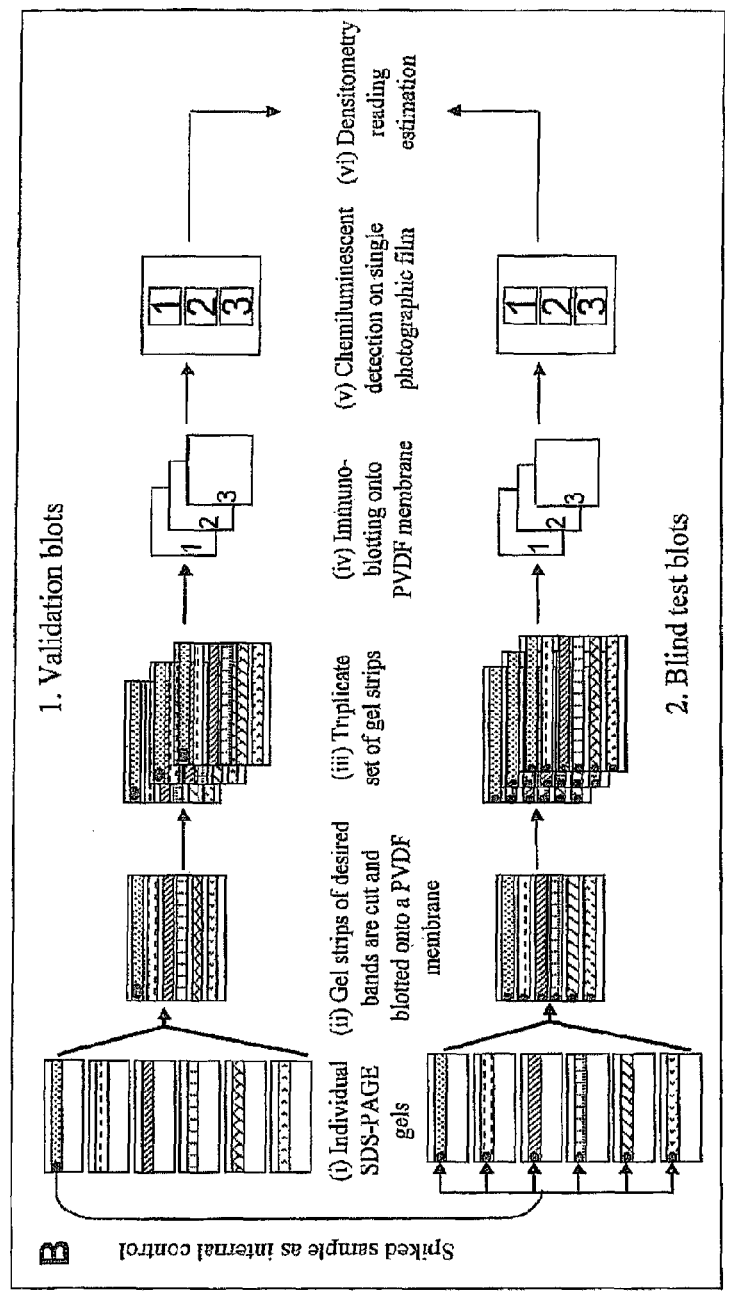
FIG. 1. (A) An overview of the workflow and experimental design of the study, including the blood collection, plasma sample preparation and the proteomics approaches used. Three iTRAQ experiments were carried out independently. (B) Illustration of the strategy used for (1) validation and (2) blind test studies of plasma samples based on C9 immunoblotting. One of the samples from the validation study (represented by black dots in the figure) was spiked into gels used for blind test to serve as an internal standard. This internal standard was used for normalization (i) within the test blots and (ii) between test and validation blots. Triplicates blots were carried out for both the validation and test blots.

A method of detecting, diagnosing or prognosing a cancer is described comprising: (a) measuring the concentration of Compliment component C9 protein (C9) in a suitable fluid sample including a body fluid sample such as blood, plasma or serum sample obtained from an individual, and (b) comparing the concentration measured in step (a) with a standard value for the concentration of Compliment component C9 protein in a suitable fluid sample of healthy individuals, wherein an increased concentration of Compliment component C9 protein as compared to the standard value for the concentration of Compliment component C9 protein from the healthy individuals is indicative for the possible presence of a cancer. The cancer may be lung cancer, gastric cancer or other types of cancer such as tumors in the bladder, brain, breast, blood, nasapharynx, uterus, cervix, colon, rectum, esophagus, mouth, head, skin, kidney, lung, ovary, neck, pancreas, prostate, testis, liver and stomach, however preferably the cancer is gastric cancer. Preferably the increase is an at least a threefold increase of the concentration of C9 protein measured in step (a) as compared to the standard value for the concentration of C9 protein of healthy individuals. The increase may be about 3 fold increase in the concentration of C9 protein in body fluids taken from an individual with early stage gastric cancer and the increase may range from about 3 fold to 45 or more fold increase in the concentration of C9 protein in body fluids taken from an individual with late stage gastric cancer or lung cancer. The suitable fluid sample may include a body fluid sample such as blood plasma, gastric juice, urine or the like. The fluid sample may have been diluted with a buffer or other reagents such as detection reagents. The individual may be any animal but preferably a human.

The method may further comprise characterizing gastric cancer intestinal type wherein an increased concentration of Compliment component C9 protein of between 3 to 4 fold as compared to the standard value for the concentration of Compliment component C9 protein in suitable fluid sample of healthy individuals is indicative of intestinal type gastric cancer. This may allow prognosis of intestinal type gastric cancer.

The method may further comprising characterizing gastric cancer diffused type wherein an increased concentration of Compliment component C9 protein of between 4 to 45 fold as compared to the standard value for the concentration of Compliment component C9 protein in the blood, plasma or serum of healthy individuals is indicative of diffused type gastric cancer. This may allow prognosis of diffused type gastric cancer.

These characterising methods have the advantage of being fast and effective way of typing gastric cancer. As the prognosis for intestinal and diffused type gastric cancer varies it is conceivable that future treatments may be developed differently for the two different types. Hence the method of using C9 expression levels to differentiate between the two types of gastric cancer will be very useful in determining which treatment would be useful and monitoring the success during the course of the treatment without repeated and excessive invasive tests.

The method may further comprising the steps of: (c) measuring the concentration of carcinoembryonic antigen (CEA) protein in the suitable fluid sample obtained from the individual, and (d) comparing the concentration measured in step (c) with a standard value for the concentration of carcinoembryonic antigen in healthy individuals; wherein an increased concentration of carcinoembryonic antigen as compared to the standard value for the concentration of carcinoembryonic antigen in healthy individuals is further indication of the possible presence of a gastric cancer.

The presence of C9 in a suitable fluid sample such as blood, plasma or serum sample can be determined by detecting the C9 protein using methods known in the art. In this invention, there are no limitations on the type of assay used to measure C9 or C9 activity. For example, C9 can be detected by immunoassays using antibodies specific for C9. The antibody being capable of binding selectively to a compliment component C9 protein and/or CEA. The antibody can be used, for example, in Western blots of one- or two-dimensional gels, in high throughput methods like enzyme linked immunoassay and/or in dot blot (Antibody Sandwich) assays of total cellular protein, or partially purified protein. Preferably, the concentration of C9 in a suitable fluid is measured by ELISA in a manner well-known in the art.

Enzyme-Linked immunosorbent Assays (ELISA) are widely used in vitro methods. In one example of the assay a serum sample is diluted 400-fold and applied to a plate to which Compliment component C9 protein (C9) antibodies from one animal origin (primary antibody) are attached. If enough C9 is present in the serum, the C9 may bind to these C9 antibodies. The plate is then washed to remove all other components of the serum. A specially prepared "secondary antibody", from an animal origin different from that of the primary antibody, an antibody that binds to the primary antibody—is then applied to the plate, followed by another wash. This secondary antibody is chemically linked in advance to an enzyme. Thus, the plate will contain enzyme in proportion to the amount of secondary antibody bound to the plate. A substrate for the enzyme is applied, and catalysis by the enzyme leads to a change in color or fluorescence. ELISA results are reported as a number; the "cut-off" point between a positive and negative result may be determined by comparing it with a known standard. Samples that generate a signal that is stronger than the known non-cancerous sample are "positive". Those that generate weaker signal than the known non-cancerous sample are "negative."

Alternatively, the concentration of Compliment component C9 protein in a suitable fluid can be determined by detecting the C9 protein using spectrometric methods such as LC-MS/MS mass spectrometer, GCMS mass spectrometer, SDS PAGE methods later quantified with densitometry or mass spectrometry methods or any similar methods of quantifying proteins known in the art.

Antibodies

The present invention also provides labelled and unlabeled monoclonal and polyclonal antibodies specific for C9 polypeptides of the invention and immortal cell lines that produce a monoclonal antibody of the invention. A preferred antibody is capable of binding selectively a Compliment component C9 protein for use in detecting gastric cancer by measuring blood, plasma or serum concentration of Compliment component C9 protein. Antibody preparation according to the invention involves: (a) conjugating a C9 polypeptide to a carrier protein; (b) immunizing a host animal with the C9 polypeptide fragment-carrier protein conjugate of step (a) admixed with an adjuvant; and (c) obtaining antibody from the immunized host animal.

According to the invention, C9 polypeptide produced recombinantly or by chemical synthesis, and fragments or other derivatives or analogs thereof, including fusion proteins, may be used as an immunogen to generate antibodies that recognize the C9 polypeptide. Such antibodies include but are not limited to polyclonal, monoclonal, chimeric, single chain, Fab fragments, and a Fab expression library.

Thus, the present invention also provides polyclonal and/or monoclonal antibodies and fragments thereof, and immunologic binding equivalents thereof, which are capable of specifically binding to the C9 polypeptides and fragments thereof or to polynucleotide sequences from the C9 polypeptide such as ISEGLPALEFPNE peptide (SEQ ID NO.: 1), particularly from the C9 gene sequence or a portion thereof. Such antibodies thus include for example, but are not limited to polyclonal, monoclonal, chimeric, single chain, Fab fragments, and a Fab expression library. Production of antibodies specific for C9 polypeptides or fragments thereof is described below.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the diagnostic, prognostic and screening methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to C9 polypeptide, or fragment, derivative or analog thereof. For the production of antibody, various host animals can be immunized by injection with the C9 polypeptide, or a derivative (e.g., fragment or fusion protein) thereof, including but not limited to rabbits, mice, rats, sheep, goats, etc. In one embodiment, the C9 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the C9 polypeptide, or fragment, analog, or derivative thereof, any technique that provides for the production of antibody molecules by continuous cell lines in culture may be used. These include but are not limited to the hybridoma technique originally developed by Kohler et al., *Nature,* 256:495-497 (1975), as well as the trioma technique, the human B-cell hybridoma technique [Kozbor et al., *Immunology Today,* 4:72 (1983)], and the EBV-hybridoma technique to produce human monoclonal antibodies [Cole et al., in *Monoclonal Antibodies and Cancer Therapy,* pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilizing recent technology (PCT/US90/02545). According to the invention, human antibodies may be used and can be obtained by using human hybridomas [Cote et al., *Proc. Natl. Acad. Sci. USA,* 80:2026-2030 (1983)] or by transforming human B cells with EBV virus in vitro (Cole et al., 1985, supra): In fact, according to the invention, techniques developed for the production of "chimeric antibodies" [Morrison et al., *J. Bacteriol.,* 159-870 (1984); Neuberger et al., *Nature,* 312:604-608 (1984); Takeda et al., *Nature,* 314:452-454 (1985)] by splicing the genes from a mouse antibody molecule specific for a C9 polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946,778) can be adapted to produce C9 polypeptide-specific single chain antibodies. An additional embodiment of the invention utilizes the techniques described for the construction of Fab expression libraries [Huse et al., *Science,* 246: 1275-1281 (1989)] to allow rapid and easy identification of monoclonal Fab fragments with the desired specificity for a C9 polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies that recognize a specific epitope of a C9 polypeptide, one may assay generated hybridomas for a product that binds to a C9 polypeptide fragment containing such epitope.

An exemplary antibody may include an affinity-purified rabbit anti-peptide LQYENVDEDSSDSDA (SEQ ID NO:4) antibody.

The foregoing antibodies can be used in methods known in the art relating to the localization and activity of the C9 polypeptide, e.g., for Western blotting, imaging C9 polypeptide in situ, measuring levels thereof in appropriate physiological samples, etc.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, a vector can be used to express the C9 polypeptide. Alternatively, one can use only hydrophilic domains to generate the fusion protein. The expressed protein will be prepared in quantity and used to immunize rabbits in Freunds adjuvant.

In yet another embodiment, recombinant C9 polypeptide is used to immunize rabbits, and the polyclonal antibodies are immunopurified prior to further use. The purified antibodies are particularly useful for semi-quantitative assays, particularly for detecting the presence of C9 polypeptide.

Preferably, the anti-modulator antibody used in the diagnostic prognostic and screening methods of this invention is an affinity-purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

In a preferred embodiment of the invention, antibodies will immunoprecipitate C9 proteins from solution as well as react with C9 protein on Western or immunoblots of polyacrylamide gels.

Preferred embodiments relating to methods for detecting C9 protein or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies.

According to the invention there is provided a diagnostic, or prognostic biomarker, C9, capable of distinguishing between gastric cancer and healthy individuals with no cancer Preferably the C9 nucleic acid comprises nucleotide sequence SEQ ID NO.:2

Preferably the C9 polypeptide comprises amino acid sequence SEQ ID NO.:3.

In preferred embodiments the concentration of Compliment component C9 protein in extracted blood, plasma or serum is used as a biomarker for gastric cancer. The Compliment component C9 protein may be a blood, plasma or serum biomarker for gastric cancer.

Aptamers

The present invention also provides aptamers specific for C9 polypeptides of the invention: A preferred aptamer is capable of binding selectively a Compliment component C9 protein for use in detecting gastric cancer by measuring blood, plasma or serum concentration of Compliment component C9 protein.

According to the invention, C9 polypeptide produced recombinantly or by chemical synthesis, and fragments or other derivatives or analogs thereof, including fusion proteins, may be used as an immunogen to generate aptamers that recognize the C9 polypeptide.

Thus, the present invention also provides aptamers and fragments thereof, and immunologic binding equivalents thereof, which are capable of specifically binding to the C9 polypeptides and fragments thereof or to polynucleotide sequences from the C9 polypeptide such as ISEGLPALEF-PNE peptide (SEQ ID NO.: 1), particularly from the C9 gene sequence or a portion thereof. Production of aptamers specific for C9 polypeptides or fragments thereof is described below.

The term "aptamer" refers to a non-naturally occurring oligonucleotide chain or peptide molecule that has a specific action on a target compound (such as a specific epitope, therapeutic drug marker or surrogate marker). A specific action includes, but is not limited to, binding of the target compound, catalytically changing the target compound, and reacting with the target compound in a way that modifies/alters the target compound or the functional activity of the target compound.

Due to its molecular recognition property, aptamers find many applications such as in cancer diagnosis and therapeutics. Cancer cells require physical interactions between different types of molecules to grow, reproduce and spread. In the area of diagnosis, aptamers that are very specific to a protein that becomes aberrant in the early stage of cancer can be used as a tool for early detection of cancer. Aptamers are also potentially less immunogenic than antibodies. Consequently, they are less likely to elicit complications such as host rejection.

Aptamers can be engineered through repeated rounds of in vitro selection or SELEX™ (systematic evolution of ligands by exponential enrichment) to bind to various molecular targets such as small molecules. Methods for production/synthesis and selection of aptamers are largely similar to that described in the following papers albeit with modifications: Ellington, A. D., Szostak, J. W., 1990. In vitro selection of RNA molecules that bind specific ligands. Nature 346, 818-822; Tuerk, C., Gold, L., 1990. Systematic evolution of ligands by exponential enrichment: RNA ligands to bacteriophage T4 DNA polymerase. Science 249, 505-510.

The "SELEX™" methodology involves the combination of selected nucleic acid ligands, which interact with a specific epitope in a desired action, for example binding to a protein, with amplification of those selected nucleic acids. Optional iterative cycling of the selection/amplification steps allows selection of one or a small number of nucleic acids, which interact most strongly with the specific epitope from a pool, which contains a very large number of nucleic acids. Cycling of the selection/amplification procedure is continued until a selected goal is achieved. The SELEX methodology is described in the following U.S. patents and patent applications: U.S. patent application Ser. No. 07/536,428 and U.S. Pat. Nos. 5,475,096 and 5,270,163.

In a preferred embodiment of the invention, aptamers will immunoprecipitate C9 proteins from solution as well as react with C9 protein on Western or immunoblots of polyacrylamide gels.

Preferred embodiments relating to methods for detecting C9 protein or its mutations include but not limited to enzyme linked immunosorbent assays (ELISA) for its high throughput nature and ease of set up and operation.

Diagnostic Kits

Detection kits may contain antibodies, amplification systems, detection reagents (chromogen, fluorophore, etc), dilution buffers, washing solutions, counter stains or any combination thereof. Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, stratifying patient populations, diagnosis, prognosis, guiding therapeutic treatment decisions, and other applications.

A preferred kit to detect a potential gastric cancer in a suitable fluid such as blood, plasma or serum sample comprises an antibody capable of binding selectively a Compliment component C9 protein and reagents for detection of a complex formed between the antibody and a complement component C9 protein. The kit may further comprise an antibody capable of binding selectively a carcinoembryonic antigen and reagents for detection of a complex formed between the antibody and CEA. The kit may further contain ELISA reagents and plates.

It is assumed that tumour specific markers are released from cancerous tissues into body fluids like the blood, plasma, serum and urine. Any of these body fluids are an ideal substrate for biomarker discovery since the acquisition process is minimally invasive and can be repeated without adverse consequences.

Figure 6A:
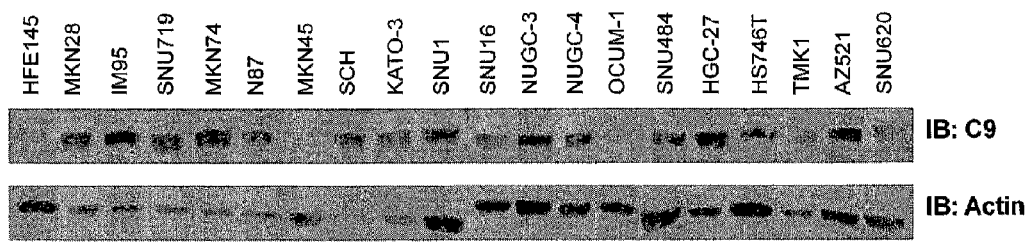
FIG. 6—Increased expression of C9 in gastric cancer cell lines. (A) Immunoblotting of C9 on the lysates of gastric cell lines. (B) Densitometry plot of the expression of C9 in the lysates of normal versus gastric cancer cell line. (C) Densitometry plot of the expression of secreted C9 in the conditioned media of normal versus gastric cancer cell line. HFE145 is a normal Gastric epithelial cell line. Immunoblotting of actin is included as loading control.
Figure 6B:
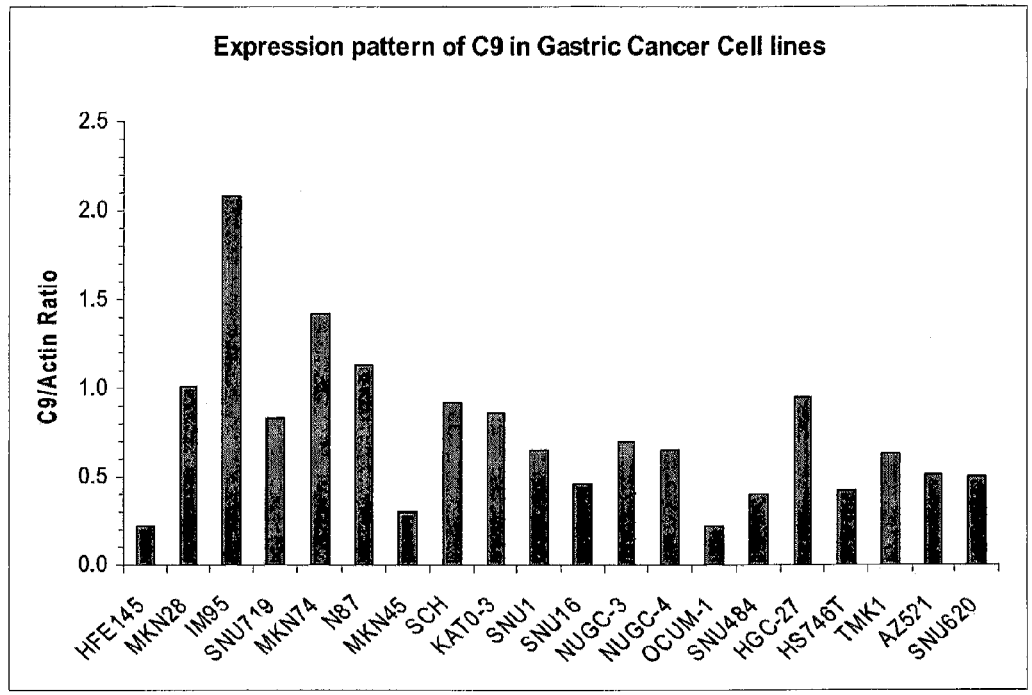
Figure 6C:
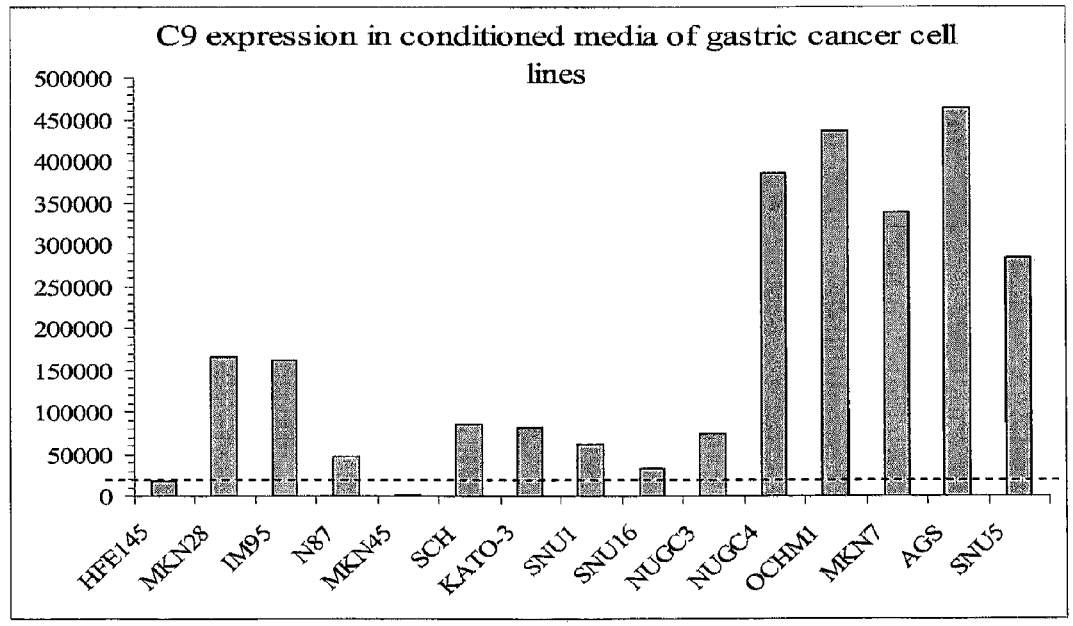

Without being limited to any theory it is conceivable that the body's immune system mounts a response to cancer cells and this led to the heightened production of C9 proteins in the blood. It is also conceivable that the elevated amount of C9 detected in the plasma of cancer patients was due to increased secretion of C9 by gastric cancer cells compared to normal cells (FIG. 6).

EXAMPLES OF PREFERRED EMBODIMENTS

Gastric cancer is one of the leading causes of cancer-related death worldwide. To date no specific marker is available in the clinic for gastric cancer screening and diagnosis. The study attempts to discover potential markers for gastric cancer by profiling the expression level of proteins in clinical plasma samples collected from normal subjects, early stage (I-II) and late stage (III-IV) of gastric cancer patients using a combination of antibody-based depletion, isotope tagging for relative and absolute quantification (iTRAQ) and tandem mass spectrometry. Samples from a total of 25 normal and 36 gastric cancer subjects were analyzed through 3 independent iTRAQ experiments.

In this study, we had employed plasma proteomics approaches for the discovery of potential biomarkers for gastric cancer. Analysis of plasma/serum based markers is one of the most attractive approaches due to the ease in sampling procedure. Our work validated C9 protein to be highly-expressed in the plasma of the majority of gastric compared to normal control. To date, elevated expression of C9 has never been reported to be associated with gastric cancer.

This study utilised Isotope Tags for Relative and Absolute Quantification (iTRAQ) to profile the levels of proteins in plasma from early and late gastric cancer stages versus normal control. The aims of the study were (i) to identify and validate proteins that have not been implicated in gastric cancer using proteomics approaches and (ii) to examine the degrees of specificity and sensitivity for gastric cancer detection by these candidates compared to CEA.

Blood Collection and Plasma Samples Preparation

Since January 2006, patients with newly diagnosed gastric cancer at both the National University Hospital and Tan Tock Seng Hospital, Singapore, have been prospectively enrolled with informed consent in a research study (Gastric Cancer Biomarker Discovery II, GASCAD II) and blood, paired normal and tumour tissue, and gastric juice samples obtained together with clinical and pathologic annotation. Blood collection was obtained before surgery or chemotherapy. Staging information was determined histopathologically and in combination with all clinical information. There was no evidence of other malignancy. American Joint Committee on Cancer (AJCC) on gastric cancer staging system and Lauren's classification on the natures of gastric cancer were used. Ethics approval had been obtained from the respective institutional review boards.

Non-cancer controls were obtained from a clinical study in which subjects had undergone screening upper gastrointestinal endoscopy which determined they were free of gastric cancer. The same blood collection protocols were used. Subjects gave informed consent and the research protocol was approved by the respective institutional review boards.

Development of the standardized protocols for blood collection and plasma preparation used by various centers involved in this study was guided by reports on the Plasma Proteome Project (PPP) (Omenn, G. S., et al., *Proteomics* 2005, 5, 3226-3245). Approximately 5 mL of blood was drawn from each patient via venipuncture into evacuated tubes coated with $K_2EDTA$ (cat#362788, Vacutainer; BD, USA). Tubes were then inverted gently for 8-times prior to standing for 30 min at room temperature. The tubes containing blood samples were kept on ice and transported to the lab. Following centrifugation at 1,100×g at 4° C. for 10 min to separate plasma from the red blood cells, protein inhibitors were added to the plasma sample and clarified by passing using 0.22 μm filter unit (Millipore, MA, USA). Plasma samples, in 1 mL aliquots were then stored in −80° C. for further analysis. To ensure the consistency in plasma preparation, a quality control measure was implemented where all the blood samples must be processed into plasma in the laboratory within an hour after blood collection in the clinic (including the min incubation at room temperature). The integrity of each plasma sample is further verified by running 1D SDS PAGE and stained with SyproRuby fluorescent dye to ensure check for massive protein degradation or sample deterioration, if any. Samples that did not satisfy the specified time frame or integrity check would be stored away but will not be used for the study.

The expressions of 37 proteins common between the 3 experiments were identified to be consistently different between the plasma of normal and cancer subjects. Using immunoblotting, the expression of complement component C9 protein was validated to be significantly higher in the plasma of gastric cancer compared to normal subjects. This observation was not due to inter-patients variations and was independent from the gastritis and *H. pylori* status of the patients. We also observed a statistically significant difference ($p<0.04$) in the expression level of C9 between patients with intestinal and diffuse types of cancer. Two independent blind test studies conducted on a total of 119 plasma samples collected from 2 different hospitals on C9 expression showed a sensitivity of 78% to 89% and specificity of 69% to 78%. The expression of C9 in sera is more sensitive than CEA which ranged from 7%-29%. This suggests the potential of C9 as a cancer marker for population screening or diagnosis as it is both sensitive and specific to gastric cancer.

Immunodetection Reagents

Mouse monoclonal C9 antibody was purchased from Abcam (Cambridge, UK). Enhanced chemiluminescence (ECL) detection kit was purchased from General Electric Healthcare, Bio-Sciences (Uppsala, Sweden); prestained molecular weight markers and acrylamide/bis-acrylamide 29:1 were from Bio-Rad (Hercules, Calif.), protease inhibitors cocktail was from Roche (Mannheim, Germany). Sodium Orthovanadate and TEMED electrophoresis reagent were purchased from Sigma Aldrich (St Louis, Mo.). The BCA protein assay kit was from Pierce (Thermo Fisher Scientific, USA), Buffers A and B used for Hu-7 depletion were purchased from Agilent Technologies (CA, USA). The sequencing grade modified trypsin was purchased from Promega (WI, USA).

Characteristics of Cohort Samples Used in this Study

We investigated 15 early stage gastric cancer patients and a range of 8 to 22 late stage patients across 3 iTRAQ experiments, as detailed in Table 1. Here we define early stage gastric cancer as those diagnosed as stages I and II based on American Joint Committee on Cancer (AJCC) staging system, whereas late stage gastric cancer were those in stages III and IV. Three independent relative quantification studies were carried out to ensure the reliability of results generated. An increasing number of sample sizes were used from the first to the third experiments owing to the sample limitation at the early phase of the project. The increasing sample sizes should produce more representative data and reduce potential biases and variations between patients. In each experiment, the number of plasma samples from normal/healthy subjects to be used as controls was the same as that used for the experimental plasma samples (gastric cancer samples). The control and test samples were matched by age and gender. The normal plasma samples were collected from healthy individuals who are cancer-free but classified as high risk in gastric cancer due to family history of gastric cancer. Plasma samples collected from 5 newly diagnosed lung cancer patients were also included in the iTRAQ-based mass spectrometry analysis study for comparison. The detailed clinical data of the samples used for iTRAQ experiments are shown in Table 1.

TABLE 1

Characteristics and clinical data of samples used in the 3 iTRAQ experiments.

| | | iTRAQ experiments | | | |
|---|---|---|---|---|---|
| Description | | 1st | 2nd | 3rd | |
| | AJCC Staging of gastric cancer | Late III-IV | Late III-IV | Early I-II | Late III-IV |
| Experimental samples | Population size | 8 | 10 | 15 | 22 |
| | Clinical data | | | | |
| | a. Gender | 7M1F | 8M2F | 8M7F | 16M6F |
| | b. Age (median) | 64.5 | 56.5 | 67 | 73 |
| | c. Ethnicity | | | | |
| | Chinese | 7 | 9 | 13 | 22 |
| | Malay | 0 | 0 | 1 | 0 |
| | Indian | 1 | 1 | 1 | 0 |
| | Others | 0 | 0 | 0 | 0 |
| | d. Lauren Classification | | | | |
| | Diffused type | 3 | 3 | 1 | 8 |
| | Intestinal type | 3 | 4 | 8 | 5 |
| | Mixed type | 1 | 1 | 1 | 4 |
| | NOS | 0 | 0 | 0 | 0 |
| | Unknown | 1 | 2 | 5 | 5 |

TABLE 1-continued

Characteristics and clinical data of samples used in the 3 iTRAQ experiments.

|  |  | iTRAQ experiments | | | |
|---|---|---|---|---|---|
|  | Description | 1st | 2nd | 3rd | |
|  | AJCC Staging of gastric cancer | Late III-IV | Late III-IV | Early I-II | Late III-IV |
|  | e. Gastritis | | | | |
|  | Positive | 4 | 5 | 15 | 22 |
|  | Negative | 2 | 3 | 0 | 0 |
|  | Unknown | 2 | 2 | 0 | 0 |
|  | f. *Helicobacter pylori* | | | | |
|  | Positive | 0 | 0 | 6 | 6 |
|  | Negative | 8 | 10 | 9 | 16 |
| Control Samples | Control population size Normal [a] | | | | |
|  | a. Sample size | 8 | 10 | 22 | |
|  | b. Gender | 7M1F | 8M2F | 16M6F | |
|  | c. Age (median) | 68.5 | 68.5 | 73 | |
|  | Lung cancer [b] | | | | |
|  | a. Sample size | N/A | N/A | 5 | N/A |
|  | b. Gender | N/A | N/A | 3M2F | N/A |
|  | c. Age (median) | N/A | N/A | 62 | N/A |

[a] The cancer-free high risk gastric cancer plasma samples were used as normal control. These samples were matched against gastric cancer samples based on the gender and age of patients.
[b] Plasma samples from newly diagnosed lung cancer patients were included as a measure of cancer specificity of potential candidates identified.

Identification and Relative Quantification of Plasma Proteins from Early and Late Stage Gastric Cancer To identify potentially novel biomarkers for gastric cancer, we profiled the expression levels of plasma proteins from gastric cancer patients using iTRAQ-based mass spectrometry approach as illustrated in FIG. 1A. The experimental samples (plasma from gastric cancer patients) in each experiment were matched to control samples based on gender and age median, as tabulated in Table 1. Plasma samples from early stage (AJCC stage I-II), late (AJCC stage III-IV) and cancer-free high risk patients were analyzed in 3 separate experiments. The methods comprised (a) removal of high abundance proteins; (b) the remaining peptides were labeled; (c) the labeled peptides were separated; (d) identified based on size of the and (d) the amount of the peptide present was quantified. The experiments used some degree of differences in their approaches. Briefly, the differences include i) the increase of samples sizes as more samples become available during the course of the project, ii) use of different depletion strategies and iii) use of mass spectrometers with different mode of ionization. Combining the data from 3 independent experiments for interpretation helped to increase the robustness of biological findings since only common proteins found in at least 2 iTRAQ experiments were taken into further consideration. Despite the small sample size, 5 plasma samples collected from lung cancer patients were also included into experiment 3 for comparison to ascertain whether a particular observation was unique to gastric cancer. The complete lists of proteins and peptides (protein summary and peptide summary) identified in each iTRAQ experiments were provided in Supplementary List 1.

Depletion of High Abundance Proteins from Plasma and iTRAQ Labeling

In all 3 iTRAQ experiments, the number of plasma samples stated in Table 1 was pooled together according to their classification (i.e. normal, early gastric cancer, late gastric cancer or lung cancer) prior to depletion of high abundance proteins. For the first and second sets of iTRAQ experiment, a total of 35 mg of protein was pooled from each sample. The pooled samples were then dilapidated by centrifugation at 130,000×g at 4° C. for 2 hr. The top transparent layer of plasma resulting from ultracentrifugation was collected and the total protein estimated using BCA assay (Pierce Biotechnology, IL, USA). Plasma samples were then subjected to depletion using IgY-12 spin column (Beckman Coulter, CA, USA) according to the manufacturer's protocol (see FIG. 1A).

In the third iTRAQ experiment, Removal System (MARS Hu-7) affinity column (Agilent Technologies, CA, USA) was used for depletion, as shown in FIG. 1A. Flow through fractions depleted of high abundance proteins were subjected to centrifugation at 4,500×g at 4° C. followed by concentration using centrifugal filter units from Millipore with a molecular weight cut-off at 5 kDa. Concentrated samples were washed 3 times with 50 mM TEAB buffer pH8.0 on the same centrifugal filter units prior to total protein estimation using BCA assay.

Protein samples were then reduced, alkylated, digested and labelled with iTRAQ reagents according to the recommended protocol (Applied Biosystems, Framingham, Mass., USA). The samples were labeled as follow: a) Experiment 1: 115—normal, 116 and 117—late gastric cancer (technical experiments), b) Experiment 2: 115—normal, 116—late gastric cancer and 117—lung cancer, a variable to provide additional information on cancer specificity of potential candidates; and c) Experiment 3: 114—normal, 115—early gastric cancer and 116—late gastric cancer.

Protein Separation LC-MS/MS Analysis for Protein Identification and Relative Quantification For iTRAQ experiments 1 and 2, the labeled peptides were subjected to matrix-assisted laser desorption ionization (MALDI)-ToF-ToF analysis for protein identification and quantification (FIG. 1A). The iTRAQ labeled peptide mixture was separated using a liquid chromatography-tandem mass spectrometry (LC-MS/MS) in this instance an Ultimate™ LC system (Dionex-LC Packings) equipped with a Probot™ MALDI spotting device, as described in our previous study (Chen, Y., et al., *Mol Cell Proteomics* 2007, 6, 2072-2087). Spotted MALDI target plates were analysed using an ABI 4700 Proteomics Analyzer MALDI-TOF/TOF mass spectrometer (Applied Biosystems, Foster City, Calif., USA) operating in a result independent acquisition model, with the same set up in our previous study (Chen, Y., et al., *Mol Cell Proteomics* 2007, 6, 2072-2087). GPS Explorer™ software version 3.5 (Applied Biosystems) was used to create and search files with the MASCOT search engine (version 2.1; Matrix Science) for peptide and protein identifications. International protein index (IPI) human database (version 3.41, date of release: March 2008, 72155 sequences) was used for the search and was restricted to tryptic peptides. Cysteine methanethiolation, N-terminal iTRAQ labeling, iTRAQ labeled-lysine, and methionine oxidation were selected as variable modifications and single miss-cleavage was allowed. Precursor error tolerance was set to 100 ppm and MS/MS fragment error tolerance to 0.3 Da. Maximum peptide rank was set to 2 and minimum ion score C.I. % (peptide) was set to 95%. The iTRAQ quantification was performed using GPS Explorer™ software version 3.5.

Conversely the dried labeled peptide mixture for 3$^{rd}$ iTRAQ experiment, re-suspended in 200 μL of Buffer A was fractionated using a PolySULFOETHYL™ A Column (PolyLC, Columbia, Md., USA) 5 μm of 200 mm length×4.6 mm ID, 200 Å pore size, on an AKTA Purifier FPLC unit (GE Healthcare, UK) with a constant flow rate of 1 mL/min and an injection volume of 200 μL. Buffer A consisted of 5 mM $KH_2PO_4$ and 30% acetonitrile, pH2.65 and Buffer B consisted of 5 mM $KH_2PO_4$, 25% acetonitrile and 350 mM KCl, pH2.65. The 55 min gradient consisted of 100% A for 5 min, 5% to 21% B for 30 min, 30% to 100% B for 15 min and 100% B for 5 min. The column was then washed with 100% Buffer C (20 mM Tris-HCl pH 8) for 10 min and re-conditioned with 100% A for 20 min. The chromatogram was monitored using UV-900 (GE Healthcare, UK) and fractions were collected every minute by Frac-950 (GE Healthcare, UK), which later were pooled together according to manual manipulation of the chromatogram profile based on the peak intensity. A total of 15 fractions were pooled. These fractions were dried in vacuum concentrator, prior to C-18 clean-up using a C18 Discovery® DSC-18 SPE column (100 mg capacity, Supelco, Sigma-Aldrich).

The dried and cleaned fractions were then analyzed using Agilent 1100 nLC system (Agilent) coupled online to a quadruple time of flight mass spectrometer (QStar XL, Applied Biosystems). SCX fractions were re-suspended in 40 μL of desalting solution containing 0.1% trifluoroacetic acid and 2% acetonitrile in water, prior loading to a reverse phase peptide Captrap (Michrom Bioresources) for desalting at 10 μL/min for 13 min. After desalting, the trap was switched on line with a 150 μm×10 cm C-18 3 μm 300 Å ProteCol column (SGE). A 120 min gradient was used, ramping from 5% to 90% Buffer B in 3 linear gradient steps to elute peptides. The column was cleaned with 100% B for 15 min and equilibrated with 100% Buffer A for 30 min prior to the next sample. Buffer A consisted of 0.1% formic acid in water and Buffer B consisted of 0.1% formic acid in 90% acetonitrile. Eluent from the reverse phase nLC was directly subjected to positive ion nanoflow electrospray analysis i.e.: electrospray ionization (ESI) in an information dependant acquisition mode (IDA), with a ToF MS survey scan was acquired (m/z 370-1600, 0.5 sec), with the 3 most intense multiple charged ions (counts >70) were sequentially subjected to MS/MS analysis. The time of summation of MS/MS events was set to be 2 sec in the mass range of m/z 100-1600.

Protein identification and quantification for iTRAQ samples were carried out using ProteinPilot™ software (version 2.0; Applied Biosystems, MDS-Sciex). The search was performed against International protein index (IPI) human database (version 3.41, date of release: March 2008, 72155 sequences). The search was performed using Paragon Algorithm™, which is discussed in detail elsewhere (Shilov, I. V., et al., *Mol Cell Proteomics* 2007, 6, 1638-1655).

Following the generation of iTRAQ ratios, a 30% cut-off value was implemented to accommodate possible technical variation, which is the main variable in the study, since biological variation is minimized by sample pooling effect. Hence, the upper and lower limit of 1.30 and 0.77, with p-value of <0.05 were applied to filter the dataset. Proteins with iTRAQ ratio above the upper limit (>1.30) were considered to be over-expressed, whereas those with ratio below the lower limit (<0.77) were considered as under-expressed. These differentially proteins were only considered significant when their p-values were below 0.05. This cut-off point is well-accepted and had been employed in other large scale protein identification and quantification studies using iTRAQ approach (Pierce, A., et al., *Mol Cell Proteomics* 2008, 7, 853-863; and Gan, C. S., et al. *Journal of proteome research* 2007, 6, 821-827). Although there is drawback in this method, which applies a general benchmark to every protein, subsequent verification step using immunoblotting will validate the key findings.

Only those proteins identified with at least 95% confidence were taken into account. All results were then exported into Excel for manual data interpretation. To ensure the reliability of the data, false positive rate was estimated by searching against a concatenated pseudo-reverse database, created in-house which consists of the forward database and their pseudo reverse sequences (Elias, J. E., Gygi, S. P., *Nature methods* 2007, 4, 207-214). Using this strategy, the false positive discovery rate (FDR) for this dataset is estimated to be approximately 1%. Here we defined FDR as the percentage of decoy proteins identified against the total protein identification. This insignificant false positive within the dataset is acceptable and tolerable.

Aforementioned, only those common proteins found across iTRAQ experiments were considered. A total of 68 common proteins were identified (data not shown) but only 37 of them were found to be differentially expressed (i.e. ratio either >1.3 or <0.77 with p-value<0.05) and their relative expression levels tabulated in Table 3. Some of these common proteins were identified with single unique peptide, which therefore has no error factor or standard deviation value except for those where the single peptide was identified with multiple MS/MS due to their presence in different LC fractions. The occurrence of single peptide hits was not surprising since plasma proteome has wide dynamic range and some proteins are of low abundance. Based on the relative ratio, these proteins were grouped into 10 expression trend clusters, as shown in Table 3. Eleven differentially expressed proteins were identified in all three iTRAQ experiments while the remaining 26 proteins were found in at least 2 of the experiments. Interestingly there were 12 proteins (in 2 trends clusters) showed either highly or under-expressed only in lung cancer, with no significant changes in gastric cancer. We did not pursue further on these proteins since lung cancer was not the primary focus of this study. Nonetheless the list might be beneficial and provide relevant information for lung cancer research.

C9 showed a similar and consistent expression trend across 3 iTRAQ experiments (see Table 3). An extract of MS/MS peptide spectrum belongs to C9 protein was illustrated in FIG. 2A, demonstrating the intensity of reporter ions belong to early and late gastric cancer samples (m/z 115 and 116 respectively) is higher compared to the normal control sample (m/z 114).

APPENDIX A

Table 3. Common proteins that showed distinct expression levels in the plasma samples from normal and cancer identified in at least 2 iTRAQ experiments.

| | | | | | | ESI-MS/MS | | MALDI-ToF-ToF | | | |
|---|---|---|---|---|---|---|---|---|---|---|---|
| | | | | | | 3rd iTRAQ | | 1st iTRAQ | | 2nd iTRAQ | |
| Trend | | | | | | Early GC Normal | Late GC Normal | late GC normal | late GC normal | late GC normal | LC normal |
| Normal | Early GC | Late GC | LC | Accession No | Gene Symbol | Protein Name | Ratio 115:114 | Ratio 116:114 | Ratio 116:115 | Ratio 117:15 | Ratio 116:115 | Ratio 117:115 |
| | | | | IPI00022426 | AMBP | AMBP protein precursor | 1.32 | 1.21 | 0.82 | 0.86 | 0.85 | 0.78 |
| | | | | IPI00022395 | C9 | Complement component C9 precursor | 1.31 | 1.74 | 1.34 | 1.31 | 1.84 | 1.60 |
| | | | | IPI00394992 | PGLYRP2 | Isoform 2 of N-acetylmuramoyl-L-alanine amidase precursor | 0.75 | 0.90 | 0.87 | 0.78 | N/A | N/A |
| | | | | IPI00022391 | APCS | Serum amyloid P-component precursor | 0.70 | 0.93 | 1.02 | 0.94 | 0.87 | 0.70 |
| | | | | IPI00847179 | APOA4 | Apolipoprotein A-IV precursor | 1.09 | 0.65 | 1.01 | 1.05 | 0.88 | 1.28 |
| | | | | IPI00744685 | BTD | Uncharacterized protein BTD (Fragment) | 0.94 | 0.69 | 1.07 | 0.74 | N/A | N/A |
| | | | | IPI00019581 | F12 | Coagulation factor XII precursor | 0.98 | 1.05 | 0.75 | 0.75 | N/A | N/A |
| | | | | IPI00010295 | CPN1 | Carboxypeptidase N catalytic chain precursor | 1.00 | 1.09 | 0.95 | 0.77 | N/A | N/A |
| | | | | IPI00022431 | AHSG | Alpha-2-HS-glycoprotein precursor | 0.91 | 0.85 | 0.64 | 0.66 | N/A | N/A |
| | | | | IPI00480192 | RBP4 | Retinol binding protein 4, plasma | N/A | N/A | 0.78 | 0.64 | 0.78 | 1.02 |
| | | | | IPI00645038 | ITIH2 | Inter-alpha (Globulin) inhibitor H2 | N/A | N/A | 0.76 | 0.77 | 0.93 | 0.98 |
| | | | | IPI00020996 | IGFALS | Insulin-like growth factor-binding protein complex acid lablle chain | 0.85 | 0.68 | 0.78 | 0.78 | 0.82 | 0.72 |
| | | | | IPI00794403 | LUM | LUM 23 kDa protein | N/A | N/A | 0.75 | 0.71 | 0.89 | 0.70 |
| | | | | IPI00645849 | ECM1 | Extracellular matrix protein 1 | 1.39 | 0.90 | N/A | N/A | 0.56 | 0.60 |
| | | | | IPI00025864 | BCHE | Cholinesterase precursor | 1.41 | 0.79 | N/A | N/A | 0.65 | 0.46 |
| | | | | IPI00019580 | PLG | Plasminogen precursor | 0.97 | 1.34 | 1.00 | 0.96 | N/A | N/A |
| | | | | IPI00032220 | AGT | Angiotensinogen precursor | 1.00 | 1.34 | 0.93 | 1.00 | 0.84 | 0.93 |
| | | | | IPI00296176 | F9 | Coagulation factor IX precursor | 1.87 | 1.41 | 1.50 | 1.23 | N/A | N/A |
| | | | | IPI00879709 | C6 | Complement component 6 precursor | 1.13 | 1.18 | 1.34 | 1.22 | 0.90 | 0.97 |
| | | | | IPI00873416 | ITIH3 | Uncharacterized protein ITIH3 | N/A | N/A | 1.97 | 1.77 | 1.05 | 1.05 |
| | | | | IPI00029739 | CFH | Isoform 1 of Complement factor H precursor | 0.84 | 0.97 | 1.26 | 1.32 | N/A | N/A |

APPENDIX A-continued

Table 3. Common proteins that showed distinct expression levels in the plasma samples from normal and cancer identified in at least 2 iTRAQ experiments.

| Trend | | | | Accession No | Gene Symbol | Protein Name | ESI-MS/MS | | | |
|---|---|---|---|---|---|---|---|---|---|---|
| | | | | | | | 3rd iTRAQ | | | |
| | | | | | | | Early GC normal | Early GC normal | Late GC Normal | Late GC Normal |
| Normal | Early GC | Late GC | LC | | | | p-Value 115:114 | EF 115:114 | p-Value 116:114 | EF 116:114 |
| | | | | IPI00022426 | AMBP | AMBP protein precursor | 0.00 | 1.17 | 0.01 | 0.15 |
| | | | | IPI00022395 | C9 | Complement component C9 precursor | 0.08 | 1.36 | 0.00 | 1.28 |
| | | | | IPI00394992 | PGLYRP2 | Isoform 2 of N-acetylmuramoyl-L-alanine amidase precursor | 0.04 | 1.32 | 0.18 | 0.16 |
| | | | | IPI00022391 | APCS | Serum amyloid P-component precursor | 0.01 | 1.29 | 0.54 | 1.26 |
| | | | | IPI00847179 | APOA4 | Apolipoprotein A-IV precursor | 0.38 | 1.21 | 0.00 | 1.12 |
| | | | | IPI00744685 | BTD | Uncharacterized protein BTD (Fragment) | 0.88 | 2.66 | 0.03 | 1.33 |
| | | | | IPI00019581 | F12 | Coagulation factor XII precursor | 0.87 | 1.47 | 0.68 | 1.33 |
| | | | | IPI00010295 | CPN1 | Carboxypeptidase N catalytic chain precursor | 0.99 | 1.38 | 0.45 | 1.36 |
| | | | | IPI00022431 | AHSG | Alpha-2-HS-glycoprotein precursor | 0.53 | 1.34 | 0.01 | 1.14 |
| | | | | IPI00480192 | RBP4 | Retinol binding protein 4, plasma | N/A | N/A | N/A | N/A |
| | | | | IPI00645038 | ITIH2 | Inter-alpha (Globulin) inhibitor H2 | N/A | N/A | N/A | N/A |
| | | | | IPI00020996 | IGFALS | Insulin-like growth factor-binding protein complex acid lablle chain | 0.47 | 1.57 | 0.02 | 1.38 |
| | | | | IPI00794403 | LUM | LUM 23 kDa protein | N/A | N/A | N/A | N/A |
| | | | | IPI00645849 | ECM1 | Extracellular matrix protein 1 | 0.16 | 1.61 | 0.45 | 1.34 |
| | | | | IPI00025864 | BCHE | Cholinesterase precursor | N/A | N/A | N/A | N/A |
| | | | | IPI00019580 | PLG | Plasminogen precursor | 0.83 | 1.36 | 0.00 | 1.18 |
| | | | | IPI00032220 | AGT | Angiotensinogen precursor | 0.97 | 1.24 | 0.04 | 1.31 |
| | | | | IPI00296176 | F9 | Coagulation factor IX precursor | N/A | N/A | N/A | N/A |
| | | | | IPI00879709 | C6 | Complement component 6 precursor | 0.47 | 1.39 | 0.19 | 1.28 |
| | | | | IPI00873416 | ITIH3 | Uncharacterized protein ITIH3 | N/A | N/A | N/A | N/A |
| | | | | IPI00029739 | CFH | Isoform 1 of Complement factor H precursor | 0.00 | 1.12 | 0.51 | 1.10 |

APPENDIX A-continued

Table 3. Common proteins that showed distinct expression levels in the plasma samples from normal and cancer identified in at least 2 iTRAQ experiments.

| Trend | | | | | Accession No | Gene Symbol | Protein Name | MALDI-ToF-ToF | | | | No of Unique peptide |
|---|---|---|---|---|---|---|---|---|---|---|---|---|
| | | | | | | | | 1st iTRAQ | | 2nd iTRAQ | | |
| | | | | | | | | late GC normal | late GC normal | late GC normal | LC normal | |
| Normal | Early GC | Late GC | LC | | | | | SD 116:115 | SD 117:115 | SD 116:115 | SD 117:115 | |
| | | | | | IPI00022426 | AMBP | AMBP protein precursor | 0.10 | 0.11 | 0.17 | 0.09 | 9 (2, 2) |
| | | | | | IPI00022395 | C9 | Complement component C9 precursor | 0.26 | 0.29 | 0.00 | 0.00 | 8 (3, 1) |
| | | | | | IPI00394992 | PGLYRP2 | Isoform 2 of N-acetylmuramoyl-L-alanine amidase precursor | 0.13 | 0.10 | N/A | N/A | 10 (2, 0) |
| | | | | | IPI00022391 | APCS | Serum amyloid P-component precursor | 0.26 | 0.10 | 0.10 | 0.16 | 7 (3, 7) |
| | | | | | IPI00847179 | APOA4 | Apolipoprotein A-IV precursor | 0.00 | 0.00 | 0.12 | 0.28 | 38 (1, 5) |
| | | | | | IPI00744685 | BTD | Uncharacterized protein BTD (Fragment) | 0.07 | 0.05 | N/A | N/A | 3 (1, 0) |
| | | | | | IPI00019581 | F12 | Coagulation factor XII precursor | 0.08 | 0.09 | N/A | N/A | 6 (2, 0) |
| | | | | | IPI00010295 | CPN1 | Carboxypeptidase N catalytic chain precursor | 0.00 | 0.00 | N/A | N/A | 4 (1, 0) |
| | | | | | IPI00022431 | AHSG | Alpha-2-HS-glycoprotein precursor | 0.00 | 0.11 | N/A | N/A | 24 (2, 0) |
| | | | | | IPI00480192 | RBP4 | Retinol binding protein 4, plasma | 0.42 | 0.17 | 0.08 | 0.01 | 0 (3, 1) |
| | | | | | IPI00645038 | ITIH2 | Inter-alpha (Globulin) inhibitor H2 | 0.05 | 0.04 | 0.22 | 0.12 | 0 (6, 5) |
| | | | | | IPI00020996 | IGFALS | Insulin-like growth factor-binding protein complex acid lablle chain | 0.22 | 0.09 | 0.16 | 0.09 | 8 (3, 8) |
| | | | | | IPI00794403 | LUM | LUM 23 kDa protein | 0.00 | 0.00 | 0.21 | 0.08 | 0 (1, 3) |
| | | | | | IPI00645849 | ECM1 | Extracellular matrix protein 1 | N/A | N/A | 0.00 | 0.00 | 6 (0, 1) |
| | | | | | IPI00025864 | BCHE | Cholinesterase precursor | N/A | N/A | 0.08 | 0.06 | 1 (1, 5) |
| | | | | | IPI00019580 | PLG | Plasminogen precursor | 0.18 | 0.12 | N/A | N/A | 15 (9, 0) |
| | | | | | IPI00032220 | AGT | Angiotensinogen precursor | 0.18 | 0.06 | 0.14 | 0.13 | 15 (2, 6) |
| | | | | | IPI00296176 | F9 | Coagulation factor IX precursor | 0.00 | 0.00 | N/A | N/A | 1 (1, 0) |
| | | | | | IPI00879709 | C6 | Complement component 6 precursor | 0.12 | 0.20 | 0.00 | 0.00 | 12 (4, 0) |
| | | | | | IPI00873416 | ITIH3 | Uncharacterized protein ITIH3 | 0.00 | 0.00 | 0.04 | 0.17 | 0 (1, 2) |
| | | | | | IPI00029739 | CFH | Isoform 1 of Complement factor H precursor | 0.16 | 0.28 | N/A | N/A | 31 (4, 0) |

APPENDIX A-continued

Table 3. Common proteins that showed distinct expression levels in the plasma samples from normal and cancer identified in at least 2 iTRAQ experiments.

| Trend | | | | Accession No | Gene Symbol | Protein Name | ESI-MS/MS | | MALDI-ToF-ToF | | | |
|---|---|---|---|---|---|---|---|---|---|---|---|---|
| | | | | | | | 3rd iTRAQ | | 1st iTRAQ | | 2nd iTRAQ | |
| | | | | | | | Early GC normal | Late GC Normal | late GC normal | late GC normal | late GC normal | LC normal |
| Normal | Early GC | Late GC | LC | | | | Ratio 115:114 | Ratio 116:114 | Ratio 116:115 | Ratio 117:115 | Ratio 116:115 | Ratio 117:115 |
| | | | | IPI00641737 | HP | Haploglobin precursor | 0.98 | 4.38 | N/A | N/A | 1.13 | 1.33 |
| | | | | IPI00847635 | SERPINA3 | Isoform 1 of Alpha-1-antichymotrypsin precursor | N/A | N/A | 1.67 | 1.64 | 1.35 | 2.37 |
| | | | | IPI00418163 | C4B | C4B1 | N/A | 1.42 | N/A | N/A | 1.31 | 1.71 |
| | | | | IPI00294193 | ITIH4 | Isoform of 1 Inter-alpha-trypsin inhibitor heavy chain H4 precursor | N/A | N/A | 0.86 | 0.97 | 1.49 | 1.84 |
| | | | | IPI00879573 | SERPIND1 | Heparin cofactor 2 precursor | N/A | N/A | 0.81 | 0.84 | 1.07 | 1.32 |
| | | | | IPI00298971 | VTN | Vitronectin precursor | 0.93 | 0.95 | 1.09 | 0.94 | 1.19 | 1.30 |
| | | | | IPI00783987 | C3 | Complement C3 precursor (Fragment) | 0.97 | 1.08 | 0.92 | 0.96 | 1.10 | 1.34 |
| | | | | IPI00470464 | ZKSCAN2 | Isoform 1 of Zinc finger protein with KRAB and SCAN domains 2 | N/A | N/A | 0.87 | 0.87 | 1.00 | 1.38 |
| | | | | IPI00742696 | GC | vitamins D-binding protein precursor | 0.78 | 0.96 | N/A | N/A | 0.83 | 0.71 |
| | | | | IPI00022371 | HRG | Histidine-rich glycoprotein precursor | 0.92 | 1.00 | 0.86 | 0.83 | 0.94 | 0.49 |
| | | | | IPI00292946 | SERPINA7 | Thyroxine-binding globulin precursor | 1.08 | 1.17 | 0.95 | 0.83 | 0.91 | 0.55 |
| | | | | IPI00011694 | PRSS1 | Trypsin-1 precursor | N/A | N/A | 0.86 | 0.94 | 0.92 | 0.43 |
| | | | | IPI00216773 | ALB | ALB protein | N/A | N/A | 0.80 | 1.07 | 0.81 | 0.48 |
| | | | | IPI00400826 | CLU | clusterin isoform 1 | 0.84 | 0.82 | N/A | N/A | 0.80 | 0.74 |
| | | | | IPI00292530 | ITIH1 | inter-alpha-trypsin inhibitor heavy chain H1 precursor | 0.90 | 0.86 | N/A | N/A | 0.93 | 0.77 |
| | | | | IPI00218795 | SELL | L-selectin precursor | N/A | N/A | 0.96 | 0.91 | 0.83 | 0.47 |

APPENDIX A-continued

Table 3. Common proteins that showed distinct expression levels in the plasma samples from normal and cancer identified in at least 2 iTRAQ experiments.

| Trend | | | | | | ESI-MS/MS | | | |
| --- | --- | --- | --- | --- | --- | --- | --- | --- | --- |
| | | | | | | 3rd iTRAQ | | | |
| | | | | Accession No | Gene Symbol | Early GC normal | Early GC normal | Late GC Normal | Late GC Normal |
| Normal | Early GC | Late GC | LC | | | p-Value 115:114 | EF 115:114 | p-Value 116:114 | EF 116:114 |
|  | | | | IPI00641737 | HP | Haptoglobolin precursor | 0.97 | 7.05 | 0.00 | 2.03 |
| | | | | IPI00847635 | SERPINA3 | Isoform 1 of Alpha-1-antichymotrypsin precursor | N/A | N/A | N/A | N/A |
| | | | | IPI00418163 | C4B | C4B1 | N/A | N/A | 0.31 | 10.87 |
| | | | | IPI00294193 | ITIH4 | Isoform of 1 Inter-alpha-trypsin inhibitor heavy chain H4 precursor | N/A | N/A | N/A | N/A |
| 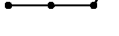 | | | | IPI00879573 | SERPIND1 | Heparin cofactor 2 precursor | N/A | N/A | N/A | N/A |
| | | | | IPI00298971 | VTN | Vitronectin precursor | 0.73 | 1.53 | 0.72 | 1.30 |
| | | | | IPI00783987 | C3 | Complement C3 precursor (Fragment) | 0.30 | 1.06 | 0.00 | 1.04 |
| | | | | IPI00470464 | ZKSCAN2 | Isoform 1 of Zinc finger protein with KRAB and SCAN domains 2 | N/A | N/A | N/A | N/A |
|  | | | | IPI00742696 | GC | vitamins D-binding protein precursor | 0.00 | 1.15 | 0.35 | 1.08 |
| | | | | IPI00022371 | HRG | Histidine-rich glycoprotein precursor | 0.12 | 1.10 | 1.00 | 1.11 |
| | | | | IPI00292946 | SERPINA7 | Thyroxine-binding globulin precursor | 0.42 | 1.25 | 0.10 | 1.23 |
| | | | | IPI00011694 | PRSS1 | Trypsin-1 precursor | N/A | N/A | N/A | N/A |
| | | | | IPI00216773 | ALB | ALB protein | N/A | N/A | N/A | N/A |
| | | | | IPI00400826 | CLU | clusterin isoform 1 | 0.01 | 1.14 | 0.03 | 1.19 |
| | | | | IPI00292530 | ITIH1 | inter-alpha-trypsin inhibitor heavy chain H1 precursor | 0.39 | 1.27 | 0.04 | 1.16 |
| | | | | IPI00218795 | SELL | L-selectin precursor | N/A | N/A | N/A | N/A |

APPENDIX A-continued

Table 3. Common proteins that showed distinct expression levels in the plasma samples from normal and cancer identified in at least 2 iTRAQ experiments.

| Trend | | | | Accession No | Gene Symbol | Protein Name | MALDI-ToF-ToF | | | | No of Unique peptide |
|---|---|---|---|---|---|---|---|---|---|---|---|
| | | | | | | | 1st iTRAQ | | 2nd iTRAQ | | |
| | | | | | | | late GC normal | late GC normal | late GC normal | LC normal | |
| Normal | Early GC | Late GC | LC | | | | SD 116:115 | SD 117:115 | SD 116:115 | SD 117:115 | |
| | | | | IPI00641737 | HP | Haptoglobolin precursor | N/A | N/A | 0.30 | 0.46 | 3 (0, 4) |
| | | | | IPI00847635 | SERPINA3 | Isoform 1 of Alpha-1-antichymotrypsin precursor | 0.38 | 0.37 | 0.43 | 1.38 | 0 (9, 13) |
| | | | | IPI00418163 | C4B | C4B1 | N/A | N/A | 0.28 | 0.61 | 1 (29, 29) |
| | | | | IPI00294193 | ITIH4 | Isoform of 1 Inter-alpha-trypsin inhibitor heavy chain H4 precursor | 0.27 | 0.20 | 0.32 | 0.47 | 0 (5, 5) |
| | | | | IPI00879573 | SERPIND1 | Heparin cofactor 2 precursor | 0.20 | 0.04 | 0.12 | 0.33 | 0 (2, 2) |
| | | | | IPI00298971 | VTN | Vitronectin precursor | 0.20 | 0.14 | 0.04 | 0.27 | 16 (5, 5) |
| | | | | IPI00783987 | C3 | Complement C3 precursor (Fragment) | 0.20 | 0.16 | 0.22 | 0.36 | 59 (52, 27) |
| | | | | IPI00470464 | ZKSCAN2 | Isoform 1 of Zinc finger protein with KRAB and SCAN domains 2 | 0.06 | 0.08 | 0.23 | 0.23 | 0 (1, 1) |
| | | | | IPI00742696 | GC | vitamins D-binding protein precursor | N/A | N/A | 0.24 | 0.17 | 32 (4, 11) |
| | | | | IPI00022371 | HRG | Histidine-rich glycoprotein precursor | 0.13 | 0.08 | 0.00 | 0.00 | 16 (6, 1) |
| | | | | IPI00292946 | SERPINA7 | Thyroxine-binding globulin precursor | 0.00 | 0.00 | 0.09 | 0.13 | 6 (1, 10) |
| | | | | IPI00011694 | PRSS1 | Trypsin-1 precursor | 0.00 | 0.00 | 0.12 | 0.04 | 0 (1, 1) |
| | | | | IPI00216773 | ALB | ALB protein | 0.05 | 0.16 | 0.03 | 0.04 | 0 (3, 1) |
| | | | | IPI00400826 | CLU | clusterin isoform 1 | N/A | N/A | 0.07 | 0.08 | 20 (0, 1) |
| | | | | IPI00292530 | ITIH1 | inter-alpha-trypsin inhibitor heavy chain H1 precursor | N/A | N/A | 0.08 | 0.10 | 33 (0, 2) |
| | | | | IPI00218795 | SELL | L-selectin precursor | 0.00 | 0.00 | 0.12 | 0.03 | 0 (1, 2) |

(i) Abbreviations: GC—Gastric cancer; LC—Lung cancer; EF—Error factor; SD—Standard deviation and N/A—not applicable.
(ii) The SD and EF values are calculated from peptides detected via MALDI and ESI platforms, respectively.
(iii) SD and EF value is not available for proteins that were identified based on single peptide, with the exception of multiple MS/MS identifications of the same peptide from different liquid chromatography fractions.
(iv) The number of unique peptides identified in ESI-MS/MS was shown as non-bracketed figure in the last column, whereas the bracketed values (x, y) represents the unique peptides identified in $1^{st}$ and $2^{nd}$ iTRAQ experiment via MALDI-MS/MS.

Immunoblotting, Validation and Blind Test Studies

To validate the expression trend of C9 revealed by iTRAQ experiments, immunoblotting was performed on the same pooled plasma samples that were used initially for proteomic analysis.

The pooled depleted plasma samples used for iTRAQ analysis were subjected to immunoblotting for C9 as described in previous studies (Lim, Y. P., et al. *Molecular cancer therapeutics* 2003, 2, 1369-1377; Lim, Y. P., et al. *The Journal of biological chemistry* 1999, 274, 19025-19034) Triplicates blots were carried out for each sample to ensure robustness of data generated. To profile the expression level of C9 in individual plasma samples, crude plasma sample (without depletion of high abundance proteins) was used for immunoblotting. Prior to this, optimized conditions for immunoblotting of C9 in crude samples were obtained by varying the protein loadings and x-ray film exposure times (data not shown). Consequently, a total of 5 μg of crude plasma protein from each sample was loaded into 1D SDS PAGE. Gel strips spanning the desired molecular weight range within which C9 migrated were cut out from various 1D gels. All the desired strips were then laid onto the same PVDF membrane and western blotted (see FIG. 1B). Triplicate PVDF membranes transferred from the triplicate runs of each plasma sample were subjected to chemiluminescence detection on a single x-ray film following immunoblotting of C9.

For densitometry, images from x-ray film were first captured using Imager Scanner and its corresponding software LabScan version 5.0 (General Electric Healthcare). Machine calibration is routinely conducted as per manusfacturer's instruction. Image was then analyzed using the 1-D gel analysis module of the ImageQuantTL software v2003.03 (General Electric Healthcare). Briefly, bands of interest were automatically detected. This was followed by manual editing of the highlighted regions so as to ensure that all bands are properly represented and without interferences from areas of non interest. Background was subtracted and the volume for each band measured.

Figure 2:
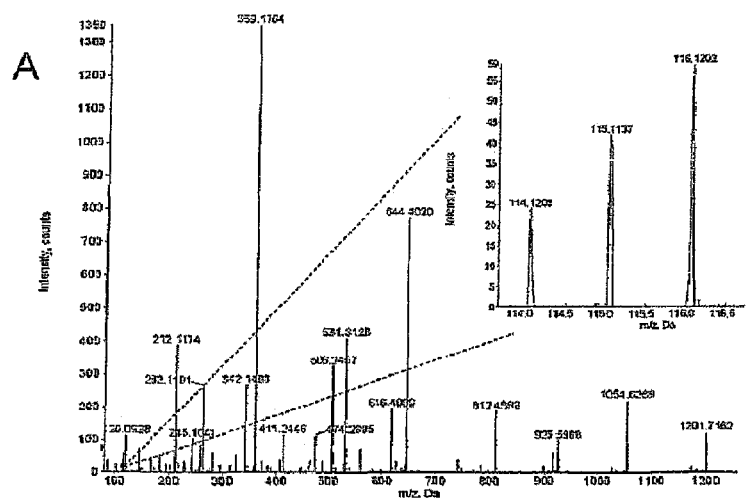
FIG. 2. (A) A representative MS/MS spectrum generated from iTRAQ experiment III illustrating the relative abundance of iTRAQ reporter ions for ISEGLPALEFPNE (SEQ ID NO:1), a doubly charged peptide with precursor mass of 780.4158 belonging to complement component C9 precursor. The relationships of the iTRAQ labels with the nature of sample are as follow: 114—normal, 115—early gastric cancer and 116—late gastric cancer. (B) The iTRAQ result and representative validation blot for C9 protein. Note: *An average ratio obtained from 3 iTRAQ experiments (with ratios of 1.34, 1.74 and 1.84) was used to illustrate the trend in late gastric cancer. Abbreviations: (i) Early GC—early gastric cancer (stage I-II), (ii) Late GC—late gastric cancer (stage III-IV) and (iii) LC—lung cancer. (C) Bar chart indicating the average densitometry reading of the C9 protein bands in the triplicate validation blots of plasma samples from early stage gastric cancer, late stage gastric cancer and lung cancer normalized against normal controls. (D) Overall protein profile of pooled plasma samples from normal control, early and late stage gastric cancer patients as well as the lung cancer subjects. Gel was stained with SYPRO Ruby to ensure equal loadings during analysis.
Figure 2:
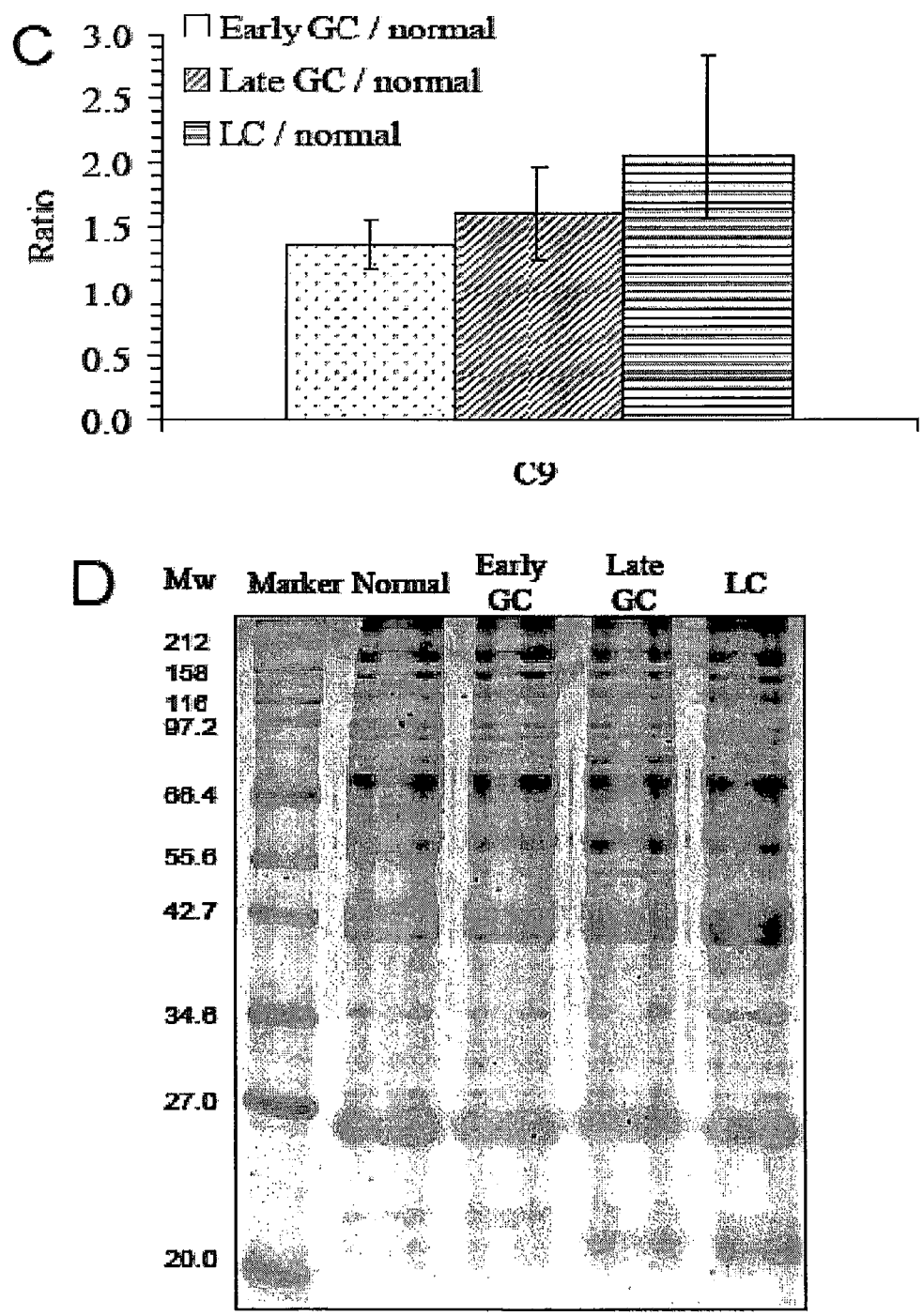

The C9 expression trend observed in immunoblots was congruent to protein expression obtained in iTRAQ approach, in which C9 was found to be over-expressed in the plasma of cancer compared to normal subjects by at least 1.3-fold (see FIGS. 2B and 2C). The overall protein expression profile obtained by staining the gel with SyproRuby fluorescent dye showed that there were equal loadings in all the lanes analyzed (FIG. 2D). Attaining consistent observations from two independent approaches (iTRAQ and immunoblotting) authenticated our findings.

The major concern and challenge dealing with clinical plasma samples is the inter-patient variations. There are numerous factors such as genetic background, diet and environmental factor that could lead to the divergence of protein expression levels between subjects. To eliminate the possibility that the higher C9 expression observed in the plasma of cancer patients compared to normal controls was due to inter-patient variation, all the samples used in the 3 independent iTRAQ analyses were individually profiled for C9 expression level through immunoblotting. In total, we screened a total of 77 samples comprising 25 normal, 15 early stage gastric cancer, 21 late stage gastric cancer and 16 lung cancer. Eleven lung cancer samples (including the 5 that were used for iTRAQ analysis) were included in this screening for comparison.

Figure 3A:
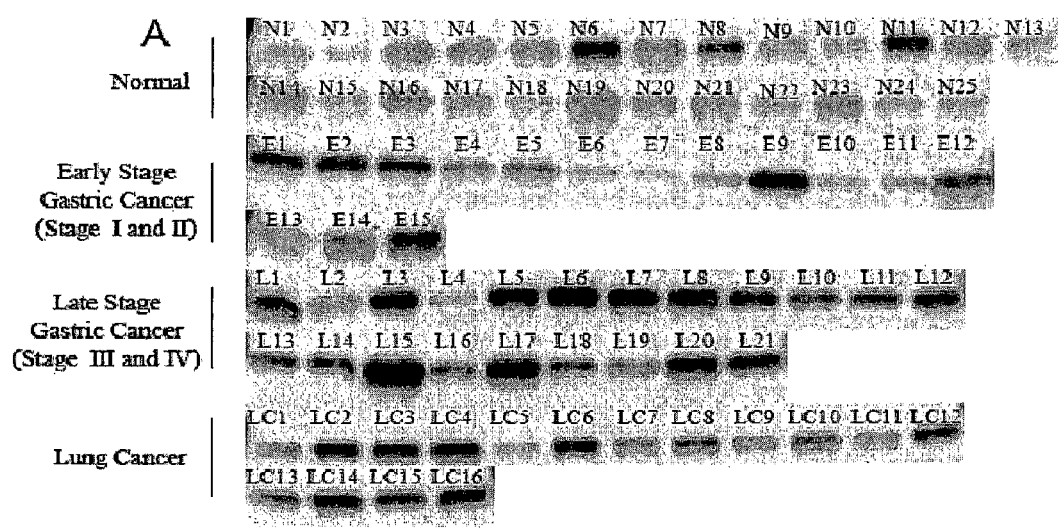
FIG. 3. (A) One of the triplicate validation blots showing the C9 expression in the individual patients used in iTRAQ experiments. An additional 11 lung cancer samples were included in the validation to increase the sample size to 16 instead of the original 5. The average densitometry readings from triplicate C9 validation blots for each sample were estimated. (B) These average readings were plotted out as a bar chart, according to the samples' nature i.e. normal, early gastric cancer (stage I-II), late gastric cancer (stage III-IV) and lung cancer groups. An average C9 densitometry reading for each sample category was also calculated and shown in the chart. (C) A box-plot showing the distribution of expression of C9 within each sample category. Analysis of variance (ANOVA) analysis was performed using the average C9 densitometry reading for each category of samples. Significant difference (p-value<0.05) in C9 expression level was observed between normal versus cancer groups (early, late stage gastric cancer and lung cancer). Abbreviations: GC=gastric cancer and LC=lung cancer.

For individual screening of C9, we decided to explore the use of crude plasma (without depletion of high abundance proteins) for immunoblotting since it is more practical and cost effective from a clinical point of view. Preliminary study showed that C9 could be detected with high confidence in crude plasma (data not shown). Therefore, triplicate immunoblots were carried out for each crude plasma samples to ensure result reproducibility. As mentioned in the "Experimental Procedures" section, immunoblotting was done by transferring various gel strips with the desired range of protein molecular weight onto a single PVDF membrane (see FIG. 1B). This procedure was repeated 3 times, generating 3 triplicate blots, which were then subjected to chemiluminescence detection. The triplicate blots were exposed simultaneously on a single x-ray film to ensure fair comparison. FIG. 3A shows an example of the triplicate blots generated for profiling C9 expression in individual plasma samples. Prior to the actual experiments, the loading amount of plasma proteins were titrated and x-ray film exposure times after chemiluminescence reaction evaluated to obtain an optimized condition/operation procedure such that the intensity of C9 signal obtained would fall within the linear range and did not suffer from saturation effect (as exemplified by FIG. 3A).

Figure 3B:
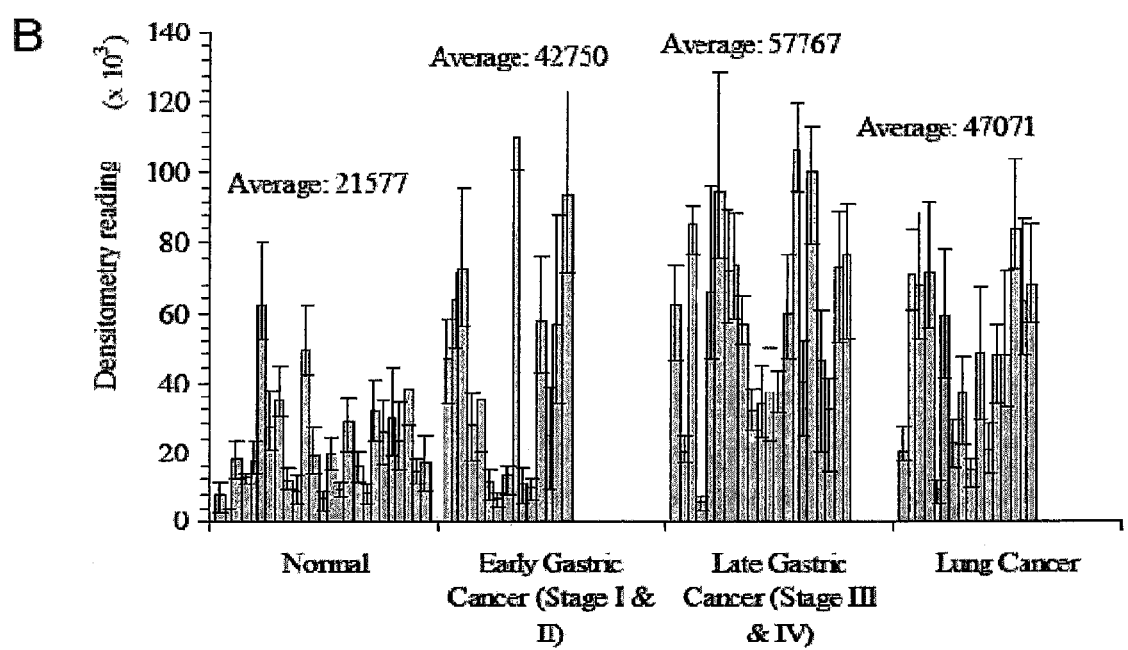
Figure 3C:
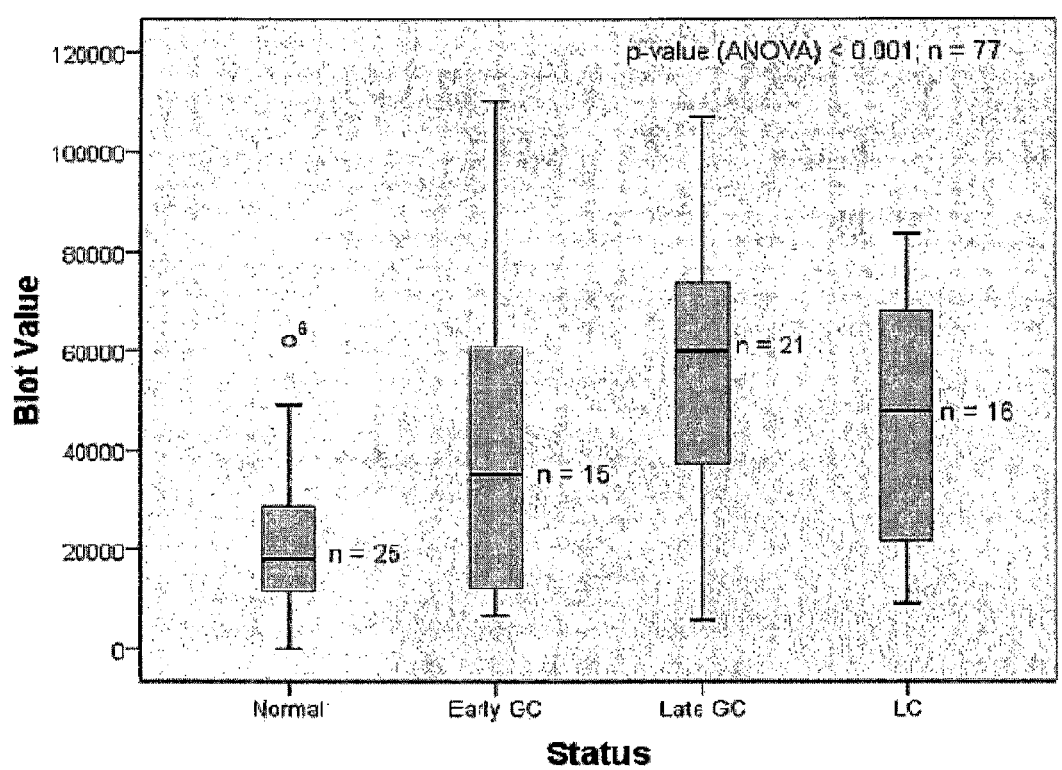

The average densitometry reading from triplicate data points for each plasma sample was calculated and plotted in FIG. 3B. The samples were grouped according to the nature of the samples, i.e. normal, early gastric cancer (stage I-II), late gastric cancer (stage III-IV) and lung cancer groups. The mean values of C9 expression level in the three cancer groups were 42750, 57767 and 47071 for early gastric cancer, late gastric cancer and lung cancer respectively. These mean values were found to be 2-fold higher compared to normal control group, which had a mean densitometry reading of 21577 (see FIG. 3B). ANOVA statistical analysis was performed to determine whether the observed difference was statistically significant. The box-plot in FIG. 3C illustrates that the differences in C9 expression is significant with p-value <0.05 when comparing the 3 cancer groups (early gastric cancer, late gastric cancer and lung cancer) to normal group. However, the expression of C9 did not have statistical power to differentiate between the 3 cancer groups.

Discriminating Between Normal and Cancer States with C9 for Blind Tests

Since C9 expression level was capable of differentiating between normal and cancer subjects with statistical confidence, we proceeded to conduct blind tests to determine whether plasma C9 levels could be used to distinguish between normal and diseased states. Two separate cohorts were engaged for the blind testing experiments to eliminate institution-derived biases. They included 64 samples from National University Hospital (NUH) and 55 samples from Tan Tock Seng Hospital (TTSH) (Table 2). These samples were selected randomly based on their availability. C9 expression level for each samples were profiled in triplicates using immunoblotting by an operator who had no prior knowledge of the samples' nature. A late stage gastric cancer patient plasma sample from the validation experiment was spiked into gels that contained the blinded samples (see FIG. 1B). This spiked sample served as an internal control for normalizing the signal density between validation and blind test blots as well within the blind test blots.

TABLE 2

Clinical data of patients from whom plasma samples were derived for blind test studies. These clinical samples were randomly selected from both National University Hospital (NUH) and Tan Tock Seng Hospital (TTSH) depending on sample availability.

| | National University Hospital (NUH) cohort | | | | Tan Tock Seng Hospital (TTSH) cohort | | | |
| --- | --- | --- | --- | --- | --- | --- | --- | --- |
| | | AJCC Staging | | | | AJCC Staging | | |
| Description | Normal | I/II (Early stage) | III/IV (Late stage) | Total | Normal | I/II (Early stage) | III/IV (Late stage) | Total |
| Total samples Clinical data | 32 | 13 | 19 | 64 | 29 | 11 | 15 | 55 |
| a. Gender | 26M8F | 8M5F | 13M6F | 47M19F | 15M10F# (4 unknown) | 7M4F | 11M4F | 33M18F |
| b. Age (median) | 62.5 | 69 | 66 | 65 | 70 | 72 | 73 | 72 |

TABLE 2-continued

Clinical data of patients from whom plasma samples were derived for blind test studies.
These clinical samples were randomly selected from both National University Hospital (NUH)
and Tan Tock Seng Hospital (TTSH) depending on sample availability.

| | National University Hospital (NUH) cohort | | | | Tan Tock Seng Hospital (TTSH) cohort | | | |
| --- | --- | --- | --- | --- | --- | --- | --- | --- |
| | | AJCC Staging | | | | AJCC Staging | | |
| Description | Normal | I/II (Early stage) | III/IV (Late stage) | Total | Normal | I/II (Early stage) | III/IV (Late stage) | Total |
| c. Ethnicity* | | | | | | | | |
| Chinese | N/A | 12 | 16 | 28 | N/A | 11 | 12 | 23 |
| Malay | N/A | 0 | 2 | 2 | N/A | 0 | 1 | 1 |
| Indian | N/A | 0 | 1 | 1 | N/A | 0 | 0 | 0 |
| Others | N/A | 1 | 0 | 1 | N/A | 0 | 2 | 2 |
| d. Lauren Classification | | | | | | | | |
| Diffused type | N/A | 2 | 6 | 8 | N/A | 1 | 2 | 3 |
| Intestinal type | N/A | 5 | 5 | 10 | N/A | 6 | 6 | 12 |
| Mixed type | N/A | 0 | 3 | 3 | N/A | 0 | 2 | 2 |
| NOS | N/A | 2 | 1 | 3 | N/A | 0 | 0 | 0 |
| Unknown | N/A | 4 | 4 | 8 | N/A | 4 | 5 | 9 |
| e. Gastritis | | | | | | | | |
| Positive | 19 | 7 | 6 | 32 | 15 | 9 | 6 | 30 |
| Negative | 11 | 6 | 12 | 29 | 6 | 1 | 8 | 15 |
| Unknown | 2 | 0 | 1 | 3 | 8 | 1 | 1 | 10 |
| f. *Helicobacter pylori* | | | | | | | | |
| Positive | 7 | 3 | 2 | 12 | 8 | 5 | 1 | 14 |
| Negative | 25 | 9 | 15 | 51 | 17 | 5 | 12 | 34 |
| Unknown | 0 | 1 | 2 | 3 | 4 | 1 | 2 | 7 |

*Ethnicity for normal controls is not available from in clinical data.
There were four normal samples collected with no specified gender given in the clinical data.

The blind tests were conducted on plasma samples collected from patients from (i) NUH Cohort—64 plasma samples collected from National University Hospital (NUH) or (ii) TTSH Cohort—55 plasma samples collected from Tan Tock Seng Hospital (TTSH). The clinical data for these two sample cohorts used for blind testing are summarized in Table 2. These blind tests were performed by operator who had no prior knowledge of the samples' nature. The immunoblotting approach used for blind testing was the same as that used in the validation step described above except that an additional reference sample comprising 5 µg of a known late gastric cancer from the validation set was spiked into the gels containing samples for blind test, acting as an internal control for densitometry scan normalization between and within test/validation blots (FIG. 1B).

Figure 4:
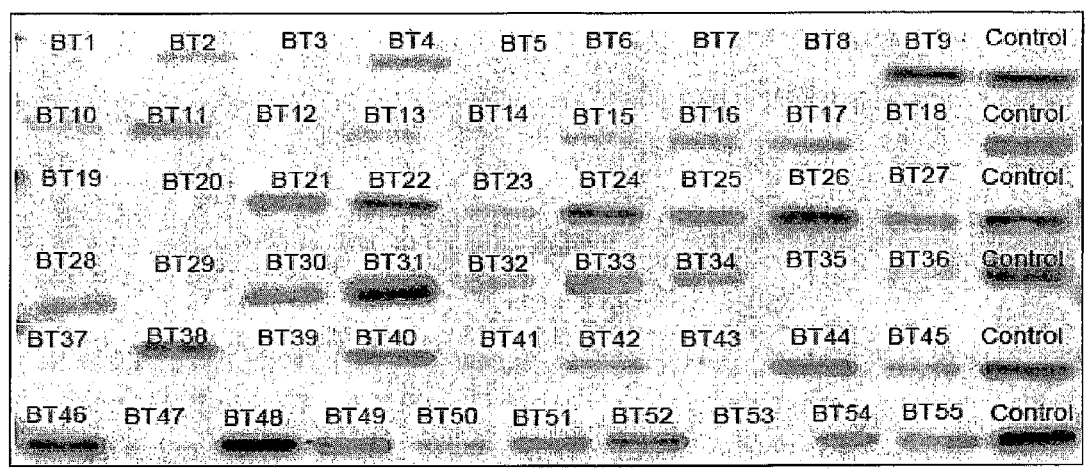
FIG. 4. A representative image from the triplicate blind tests carried out on plasma samples from Tan Tock Seng Hospital (TTSH) cohort. A total of 55 blinded samples were examined for C9 expression. A sample from the validation study was spiked into the analytical gels to serve as an internal standard for normalization (i) across the triplicate blind test blots and (ii) between validation blots and test blind blots.

Similar to the validation process, average densitometry reading for each sample was calculated from the triplicate data points. FIG. 4 shows one of the triplicate blots from the blind test conducted on the NUH cohort. Sample was then predicted to be either normal, early gastric cancer or late gastric cancer based on the mean C9 densitometry reading cut-off value predicted in the validation blots. As mentioned previously, the average densitometry reading for normal, early and late stage gastric cancer from the validation blots were 21577, 42750 and 57767 respectively. These values were used as the cut-off values for blind test prediction—samples with average densitometry reading of (i) <21577 were predicted as normal, (ii) between the range of 21577-42750 were early gastric cancer and (iii) >42750 were late gastric cancer. Using this cut-off scheme, approximately 66% (42 out of 64) and 69% (38 out of 55) of the samples were predicted correctly, matched with their staging in clinical data for NUH cohort (Table 4A) and TTSH cohort (Table 4B) respectively. In the NUH cohort, C9 specificity was estimated to be approximately 78%, i.e. 9% higher compared to 69% estimated from TTSH cohort. C9 was found to be less sensitive for early gastric cancer where its sensitivity was found to be 31% in NUH cohort and 46% in TTSH cohort. In contrast, C9's sensitivity towards late stage gastric cancer was significantly higher; i.e. 68% and 87% for NUH and TTSH cohorts, indicating C9 has greater potential in identifying advance stages of gastric cancer. If cancer stages were not taken into account, C9's sensitivity improved to 78% and 89% for NUH and TTSH cohorts, respectively. This illustrates C9 has considerable specificity and sensitivity in discriminating between plasma from (i) cancer patients and (ii) cancer patients with advanced stage of cancer from normal subjects.

TABLE 4

Use of C9 expression level for blind test studies of samples from 2 independent medical centers prediction i.e. (A) National University Hospital (NUH) cohort and (B) Tan Tock Seng Hospital (TTSH) cohort. C9 sensitivity and specificity in detecting gastric cancer was determined. (C) In comparison, carcinoembryonic antigen (CEA) levels were measured for plasma samples used in validation set and 55 randomly selected samples from both NUH and TTSH blind test cohorts. Sensitivity and specificity of CEA for gastric cancer prediction was then calculated.

| | Sample prediction based on average densitometry cut-off[a] | | | | | | |
|---|---|---|---|---|---|---|---|
| | No of samples correctly predicted | No of samples wrongly predicted | Total sample prediction | Percentage of right prediction (%) | Percentage of wrong prediction (%) | C9 sensitivity (%) | C9 Specificity (%) |
| A. Plasma samples from NUH cohort | | | | | | | |
| Normal | 25 | 7 | 32 | 78.1 | 21.9 | N/A | 78.1 |
| Early gastric cancer (stage I-II) | 4 | 9 | 13 | 30.8 | 69.2 | 30.8 | |
| Late gastric cancer (stage III-IV) | 13 | 6 | 19 | 68.4 | 31.6 | 68.4 | |
| Gastric cancer (stage I-IV)[b] | 25 | 7 | 32 | 78.1 | 21.9 | 78.1 | |
| B. Plasma samples from TTSH | | | | | | | |
| Normal | 20 | 9 | 29 | 69.0 | 31.0 | N/A | 69.0 |
| Early gastric cancer (stage I-II) | 5 | 6 | 11 | 45.5 | 54.5 | 45.5 | |
| Late gastric cancer (stage III-IV) | 13 | 2 | 15 | 86.7 | 13.3 | 86.7 | |
| Gastric cancer (stage I-IV)[b] | 23 | 3 | 26 | 88.5 | 11.5 | 88.5 | |

[a]The average densitometry reading cut-offs used for sample prediction were: (i) normal < 21577, (ii) 21577 < early gastric cancer (stage I-II) < 42750, (iii) late gastric cancer (stage III-IV) > 42750 and (iv) all stages of gastric cancer > 21577.
[b]This included early and late stage gastric cancer samples.

*Helicobacter pylori* infection is one of the strongest risk factors associated with gastric cancer (Peek, R. M., Jr., Blaser, M. J., *Nature reviews* 2002, 2, 28-37) while gastritis is not uncommon in gastric cancer patients. To determine whether the diagnostic value of C9 was influenced by these clinical parameters, we asked whether the 2 groups of samples correctly predicted to be of normal (45 out of 61) or cancer (48 out of 58) status had distinctive *H. pylori* or gastritis status. Statistical analyses showed negative results (see Table 5). This indicates that the diagnostic value of C9 between normal and gastric cancer plasma was not affected by inflammation or infection status of the subjects tested.

Carcinoembryonic Antigen (CEA) Screening

In the clinical setting, CEA is routinely used as marker for gastrointestinal carcinoma (Crepaldi-Filho, R., et al., *Arquivos de gastroenterologia* 2008, 45, 219-224). CEA screening in this study was performed by a professional medical diagnostic lab that is housed within the National University Hospital and accredited by Ministry of Health Singapore. Only a total of 115 out of 183 samples (all 61 samples from validation set and 54 randomly selected samples from both blind test cohorts) were sent for CEA screening to reduce cost. The reference value for CEA is <5 μg/L, which was also used in another study (Bel Hadj Hmida, Y., et al., *La Tunisie medicale* 2001, 79, 434-440). Any sample that fell below this reference value was considered normal.

Two set of plasma samples including (i) all the 61 samples from validation set and (ii) 54 plasma samples, randomly selected from both NUH and TTSH cohort samples used for blind testing, were tested for the presence of CEA. A standardized CEA analysis was performed on these samples by trained personnel. Briefly, ADVIA Centaur CEA assay (Siemens Healthcare Diagnostics), a two-site sandwich immunoassay using direct chemiluminometric technology, was employed. Two antibodies were used in the assay—(i) a purified polyclonal rabbit anti-CEA antibody labeled with acridinium ester (Siemens ADVIA Centaur Ready Pack, Primary reagent pack, Lite Reagent) and (ii) a monoclonal mouse anti-CEA antibody covalently coupled to paramagnetic particles (Siemens ADVIA Centaur Ready Pack, Primary reagent pack, Solid Phase). These two antibodies and 50 µL of plasma sample were added into the cuvettes and incubated at 37° C. for 7.5 min, prior to washing with water. Acid and Base reagents were then added into the cuvettes to initiate the chemiluminescent reaction. The amount of CEA presents in the sample has a direct relationship with the amount of relative light units (RLUs) detected. The total duration of the assay is 18 min and in a fully automated way. The CEA reference range used in this diagnostic lab is 0.0 to 0.5 µg/L. Any reading that falls within this reference range is considered normal.

It is not surprising that CEA specificity was 100% for both validation and blind test set, as similar observation was reported (Hao, Y., et al., *Journal of proteome research* 2008, 7, 3668-3677). However CEA sensitivity was very poor ranging from 7% to 13% for early gastric cancer and 18% to 29% for late stage gastric cancer, whereas for all stages of gastric cancer, the sensitivity ranged between 16% to 19% (see Table 4C). This sensitivity range obtained is consistent with existing figures (Ebert, M. P., Rocken, C., *European journal of gastroenterology & hepatology* 2006, 18, 847-853).

TABLE 4C

| C. Samples used for | Plasma samples | CEA Limits | No of samples correctly predicted | No of samples wrongly predicted | Total sample prediction | Percentage of right prediction (%) | Percentage of wrong prediction (%) | CEA sensitivity (%) | CEA specificity (%) |
|---|---|---|---|---|---|---|---|---|---|
| Validation set | Normal | 0-5 µg/L | 25 | 0 | 25 | 100% | 0% | N/A | 100% |
| | Early gastric cancer (stage I-II) | >5 µg/L | 1 | 14 | 15 | 7% | 93% | 7% | |
| | Late gastric cancer (stage III-IV) | >5 µg/L | 6 | 15 | 21 | 29% | 71% | 29% | |
| | Gastric cancer (stage I-IV) | >5 µg/L | 7 | 29 | 36 | 19% | 81% | 19% | |
| Blind test set | Normal | 0-5 µg/L | 29 | 0 | 29 | 100% | 0% | N/A | 100% |
| | Early gastric cancer (stage I-II) | >5 µg/L | 1 | 7 | 8 | 13% | 88% | 13% | |
| | Late gastric cancer (stage III-IV) | >5 µg/L | 3 | 14 | 17 | 18% | 82% | 18% | |
| | Gastric cancer (stage I-IV) | >5 µg/L | 4 | 21 | 25 | 16% | 84% | 16% | |

Use of C9 to Differentiate Between Gastric Cancer Types

Figure 5:
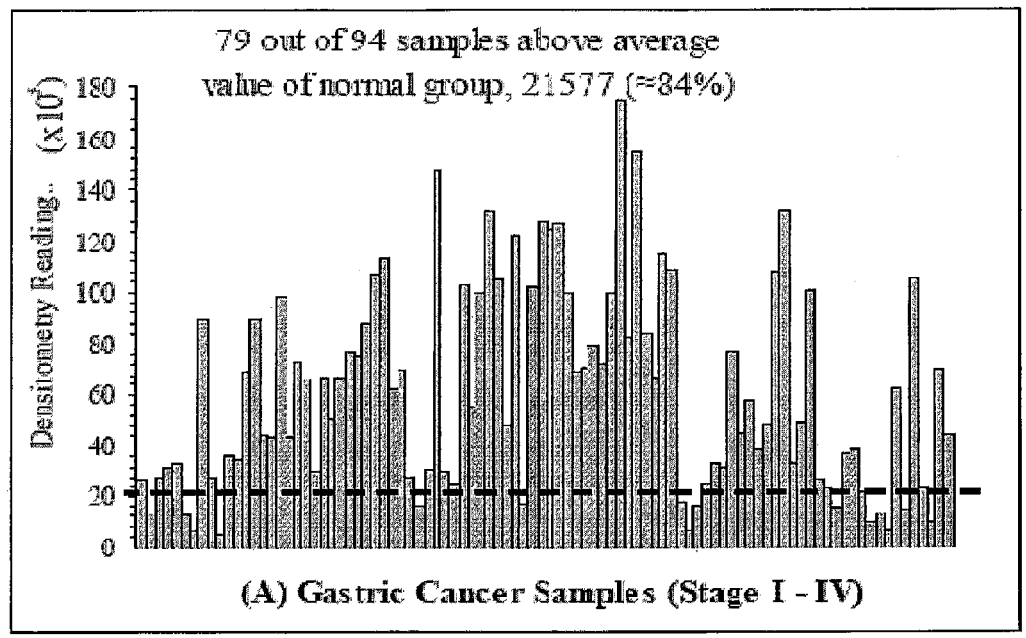
FIG. 5. C9 expression in all the individual plasma samples used in this study (validation+blind tests). Bar charts illustrate the densitometry reading of C9 protein band after immunoblotting of plasma samples from (A) all gastric cancer samples (early and late i.e. stage I-IV), (B) early gastric cancer (stage I-II), (C) late gastric cancer (stage III-IV) and (D) lung cancer samples analyzed in both validation and blind test blots. (E) Scatter plot showing the C9 expression levels in plasma samples from patients whose cancers were classified into diffused, intestinal or mixed type of gastric cancer. The dotted lines indicate the average value of C9 blot expression in the plasma from normal controls.
Figure 5:
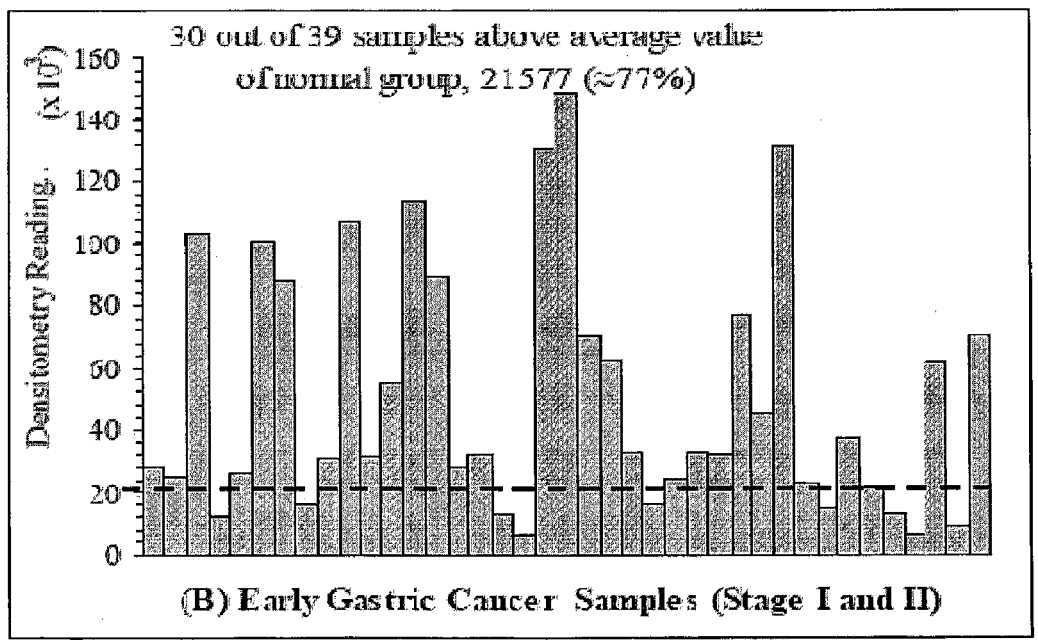
Figure 5:
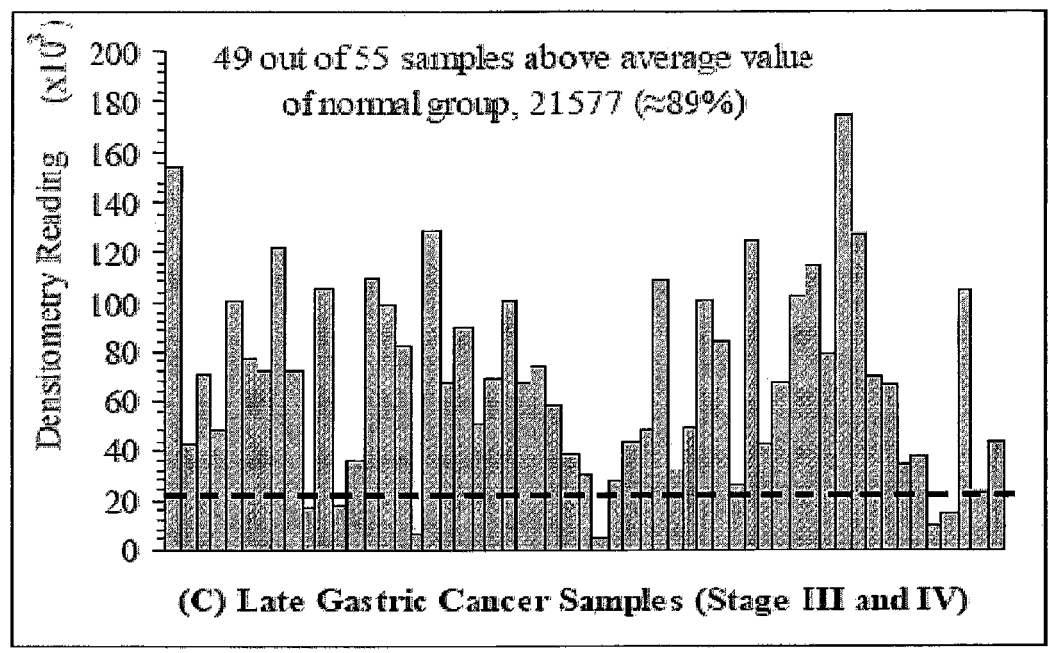
Figure 5:
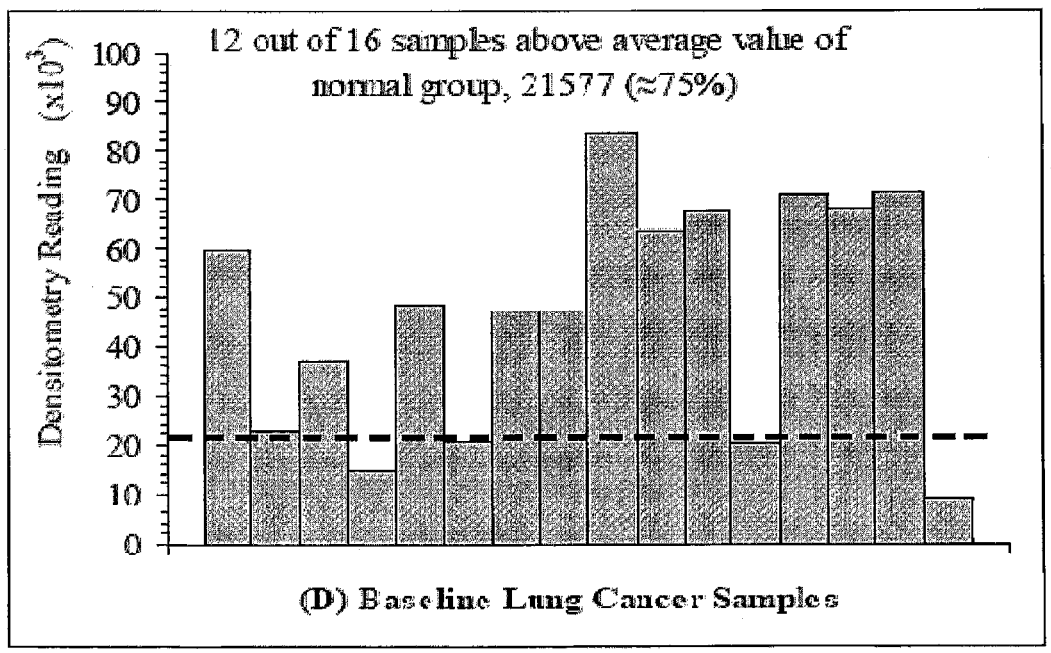
Figure 5E:
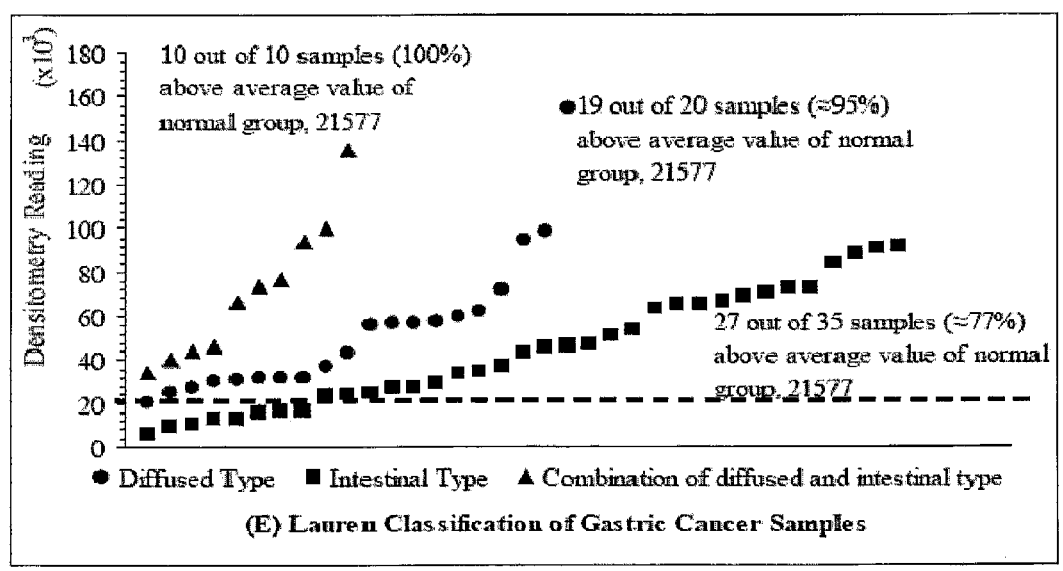

Our study showed 95% (out of 20) of the diffuse type gastric cancer patients had high C9 expression level in plasma sample (FIG. 5E). High C9 expression was also found in 77% out of 35 intestinal type gastric cancer patients. There were 10 patients who were diagnosed with a combination of both diffuse and intestinal type gastric cancer, and all of them had high C9 expression level in plasma. ANOVA and post-hoc statistical analysis revealed that a statistically significant p-value of <0.04 could be obtained when differentiation between the diffused and intestinal type of gastric cancer based on plasma C9 expression was attempted (see Table 5). It is clinically relevant as the symptoms of diffuse gastric cancer are rather non-specific and hence the diagnosis is difficult and often late, compared to the intestinal type.

TABLE 5

Statistical correlation of C9 expression level with Lauren's classification of gastric cancer subtypes and other analyses. There was no significant distinction in *H. pylori* or gastritis status between 2 sample groups i.e. correctly predicted normal and correctly predicted cancer samples in blind test cohorts. In contrast, C9 expression in plasma samples from all cancer patients was demonstrated to be correlate significantly with Lauren classification with p-value < 0.05.

| Dataset | Sample Type | Clinical data | Sample size | Statistical analysis | p-value |
|---|---|---|---|---|---|
| Blind tests (NUH and TTSH cohorts) | [a]Correct sample prediction (Normal and Cancer) | H. Pylori+/− | 93[b] | chi-square test | 0.263 |
| | | Gastritis+/− | 93[b] | chi-square test | 0.397 |
| Validation and blind tests (NUH and TTSH cohorts) | Cancer samples | Lauren classification | 65[c] | ANOVA | 0.040 |
| | | | 55[d] | Post-hoc (Diffused and intestinal) | 0.035 |

[a]Include only those samples that were corrected predicted to be normal and cancer samples based on their C9 expression level.
[b]Samples consisted of 45 correctly predicted normal samples and 48 correctly predicted cancer samples.
[c]Samples included 20, diffused, 35 intestinal and 10 combination of both diffuse and intestinal type gastric cancer.
[d]Only 20 diffused and 35 intestinal type gastric cancer were considered.

Statistical analyses were carried out using both asymmetric and non-asymmetric analysis including ANOVA, chi-square test and post-hoc analysis. All these analyses were performed at 5% significant using statistical software SPSS 16.0 for Windows. ANOVA analysis was carried out to investigate statistically differences in C9 expression level obtained via immunoblot in normal plasma compared to cancer plasma. To investigate *Helicobacter pylori* infection (HP+/−) and gastritis infection (+/−) status between the correctly predicted normal and correctly predicted cancer samples based on C9 expression level, chi-square test was employed. On the other hand, correlation between C9 expressions level with Lauren classification (Diffused, intestinal or combination of both) was calculated using ANOVA and Post-hoc analysis.

Profiling of C9 Expression Across Individual Plasma Samples from Cancer Patients When all the 94 individual plasma samples (used in validation and blind tests) from gastric cancer patients were plotted for C9 expression, 84% (79/94) of these samples showed high expression level of C9 as defined by densitometry value of >21577 units (FIG. 5A). Among these samples, 39 were early stage gastric cancer samples (stage I-II) and 55 were late stage gastric cancer samples (stage III-IV). Approximately 77% (30/39) and 89% (49/55) of the early and late stage gastric cancer samples showed high C9 expression levels, respectively (FIGS. 5B and 5C). This is consistent with a report on multiple myeloma patients that while the classical and alternative pathways were activated in most patients in early and late stages, the terminal pathway (involving C5 to C9) was more frequently activated in the later stages (7 of 12 patients) (Lugassy, G., et al., *Leuk Lymphoma* 1999, 33, 365-370).

Possible Mode of C9 Elevation in Plasma of Cancer Patients—Indications and Contraindications It is conceivable that the body's immune system mounts a response to cancer cells and this led to the heightened production of C9 proteins in the blood. This also implies that over-expression of C9 in plasma is not limited to gastric cancer. Indeed, this was not the case as high level of C9 was observed in 75% of lung cancer plasma samples in our study as well as in the blood of acute leukemia and sarcoma (Lichtenfeld, J. L., et al., *Cancer research* 1976, 36, 3678-3680).

In contrast, Cheng and colleagues reported the up-regulation of C9 gene expression in esophageal adenocarcinoma compared to normal epithelial cells. In our study, we also detected increased intracellular and extracellular C9 levels in a panel of gastric cancer cell lines compared to normal cell line (FIG. 6). This suggests that elevation of C9 could be cancer specific and not merely an immune response. The mechanism behind the elevation of plasma C9 levels in gastric cancer remains to be clarified.

The current screening method using immunoblotting is expensive, time-consuming, labor intensive, low throughput and most importantly prone to technical variability and is at best semi quantitative. To conduct future studies to validate the clinical utility of C9 for gastric cancer diagnosis on a larger sample size, ELISA should be developed to achieve a higher throughput, more consistent and quantitative assay.

With reference to these statements, our findings from the blind tests conducted on more than 100 samples from 2 separate hospital cohorts, indicate that C9 has a sensitivity of 78% to 86% for gastric cancer detection. The specificity of C9 for gastric cancer ranged from 69% to 78%, which was lower than CEA. For this reason a combination test detecting both C9 and CEA is sera is both sensitive and specific providing a very useful screening method for gastric cancer.

Given the heterogeneous nature of cancer, it is not surprising that different markers may be combined for improved cancer detection. In conclusion, C9 is a potential candidate for gastric cancer detection. While the heightened level of C9 was not associated with gastritis in our study and might be a result of higher level of C9 secreted by gastric cancer cells (FIG. 6), higher sera C9 level could also be observed in patients with immune disorders such as rheumatoid arthritis and auto-immune diseases (Kawachi-Takahashi, S., et al., *International archives of allergy and applied immunology* 1975, 48, 161-170; Kawachi-Takahashi, S., et al., *The Japanese journal of experimental medicine* 1974, 44, 845-847; Oleesky, D. A., et al., *Clinical endocrinology* 1986, 25, 623-632; Rumfeld, W. R., et al., *British journal of rheumatology* 1986, 25, 266-270; Greenstein, J. D., et al., *Clinical and experimental immunology* 1996, 104, 160-166). These observations raised a cautionary note that C9 as a diagnostic marker should be used with care and interpretation of results should taken into account of the medical history/background of patients especially those with immune disorders. It also means that C9 most suitable for targeted screening i.e, subjects with high risk to gastric cancer and may be considered for inclusion into a combinatorial approach for cancer detection using molecular cancer markers.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with reference to specific methods and embodiments, it will be appreciated that various modifications and changes may be made without departing from the invention.

The invention claimed is:

1. A method of detecting the presence of a gastric cancer in an individual suspected or at risk of having gastric cancer, the method comprising:
   (a) measuring, with an antibody, the concentration of Complement component C9 protein in a blood, plasma or serum sample obtained from an individual suspected or at risk of having gastric cancer, wherein the Complement component C9 protein comprises the amino acid sequence of SEQ ID NO:3, and wherein the antibody specifically binds to the amino acid sequence of SEQ ID NO:1,
   (b) comparing the concentration measured in step (a) with a standard value range for the concentration of Complement component C9 protein in blood, plasma or serum of healthy individuals, and
   (c) determining that the individual has or is at risk of having gastric cancer when the concentration of Complement component C9 in the blood, plasma or serum sample of the individual is increased in comparison to the standard value range for the concentration of Complement component C9 protein in blood, plasma or serum of healthy individuals.

2. The method of claim 1 further comprising the steps of:
   (d) measuring the concentration of carcinoembryonic antigen protein in the blood, plasma or serum sample obtained from the individual,
   (e) comparing the concentration measured in step (d) with a standard value for the concentration of carcinoembryonic antigen in blood, plasma or serum of healthy individuals, and
   (f) determining that the individual has or is at risk of having gastric cancer when the concentration of carcinoembryonic antigen protein in the blood, plasma or serum sample of the individual is increased in comparison to the standard value for the concentration of carcinoembryonic antigen in blood, plasma or serum of healthy.

3. The method of claim 2, wherein said concentration of carcinoembryonic antigen is measured using an antibody capable of binding selectively to a carcinoembryonic antigen.

4. The method of claim 2, wherein said concentration of carcinoembryonic antigen is measured spectrophotometrically.

5. The method of claim 1, wherein said concentration of Complement component C9 protein is measured by ELISA.

6. The method of claim 1 further comprising characterizing gastric cancer as intestinal type gastric cancer when the blood, plasma or serum sample of the individual has an increased concentration of Complement component C9 protein of between 3 to 4 fold as compared to the standard value for the concentration of Complement component C9 protein in blood, plasma or serum of healthy individuals.

7. The method of claim 1 further comprising characterizing gastric cancer as diffused type gastric cancer when the blood, plasma or serum sample of the individual has an increased concentration of Complement component C9 protein of between 4 to 45 fold as compared to the standard value for the concentration of Complement component C9 protein in blood, plasma or serum of healthy individuals.

8. The method of claim 1, wherein the antibody is a monoclonal antibody.

9. The method of claim 1, wherein the increase of the concentration of Complement component C9 protein is at least a 3 fold increase as compared to the standard value range for the concentration of Complement component C9 protein in blood, plasma or serum of healthy individuals.

10. The method of claim 9, further comprising:
(d) measuring the concentration of carcinoembryonic antigen protein in the blood, plasma or serum sample obtained from the individual,
(e) comparing the concentration measured in step (d) with a standard value for the concentration of carcinoembryonic antigen in blood, plasma or serum of healthy individuals, and
(f) determining that the individual has or is at risk of having gastric cancer when the concentration of the carcinoembryonic antigen in the blood, plasma or serum sample of the individual is increased in comparison to the standard value for the concentration of carcinoembryonic antigen in blood, plasma or serum of healthy individuals.

* * * * *

```
                        SEQUENCE LISTING

<160> NUMBER OF SEQ ID NOS: 4

<210> SEQ ID NO 1
<211> LENGTH: 13
<212> TYPE: PRT
<213> ORGANISM: Homo sapiens

<400> SEQUENCE: 1

Ile Ser Glu Gly Leu Pro Ala Leu Glu Phe Pro Asn Glu
1               5                   10

<210> SEQ ID NO 2
<211> LENGTH: 2693
<212> TYPE: DNA
<213> ORGANISM: Homo sapiens

<400> SEQUENCE: 2
gcttgttccc tgtcctctgg ccctttgcaa ataaatgcct taccagacct gccctgccac      60
cccactcgca gccacccagc aagagcagca tgtcagcctg ccggagcttt gcagttgcaa     120
tctgcatttt agaaataagc atcctcacag cacagtacac gaccagttat gacccagagc     180
taacagaaag cagtggctct gcatcacaca tagactgcag aatgagcccc tggagtgaat     240
ggtcacaatg cgatccttgt ctcagacaaa tgtttcgttc aagaagcatt gaggtctttg     300
gacaatttaa tgggaaaaga tgcaccgacg ctgtgggaga cagacgacag tgtgtgccca     360
cagagccctg tgaggatgct gaggatgact gcggaaatga ctttcaatgc agtacaggca     420
gatgcataaa gatgcgactt cggtgtaatg gtgacaatga ctgcggagac ttttcagatg     480
```

```
aggatgattg tgaaagtgag ccccgtcccc cctgcagaga cagagtggta gaagagtctg    540
agctggcacg aacagcaggc tatgggatca acattttagg gatggatccc ctaagcacac    600
cttttgacaa tgagttctac aatggactct gtaaccggga tcgggatgga aacactctga    660
catactaccg aagaccttgg aacgtggctt ctttgatcta tgaaaccaaa ggcgagaaaa    720
atttcagaac cgaacattac gaagaacaaa ttgaagcatt taaaagtatc atccaagaga    780
agacatcaaa ttttaatgca gctatatctc taaaatttac acccactgaa acaaataaag    840
ctgaacaatg ttgtgaggaa acagcctcct caatttcttt acatggcaag ggtagttttc    900
ggttttcata ttccaaaaat gaaacttacc aactattttt gtcatattct tcaaagaagg    960
aaaaaatgtt tctgcatgtg aaaggagaaa ttcatctggg aagatttgta atgagaaatc    1020
gcgatgttgt gctcacaaca acttttgtgg atgatataaa agcttgcca actacctatg    1080 aaaagggaga atattttgcc ttttt ggaaa cctatggaac tcactacagt agctctgggt    1140
ctctaggagg actctatgaa ctaatatatg ttttggataa agcttccatg aagcggaaag    1200
gtgttgaact aaaagacata aagagatgcc ttgggtatca tctggatgta tctctggctt    1260
tctctgaaat ctctgttgga gctgaattta ataaagatga ttgtgtaaag aggggagagg    1320
gtagagctgt aaacatcacc agtgaaaacc tcatagatga tgttgtttca ctcataagag    1380
gtggaaccag aaaatatgca tttgaactga agaaaagct tctccgagga accgtgattg    1440
atgtgactga cttt gtcaac tgggcctctt ccataaatga tgctcctgtt ctcattagtc    1500
aaaaactgtc tcctatatat aatctggttc cagtgaaaat gaaaaatgca cacctaaaga    1560
aacaaaactt ggaaagagcc attgaagact atatcaatga atttagtgta agaaaatgcc    1620
acacatgcca aaatggaggt acagtgattc taatggatgg aaagtgtttg tgtgcctgcc    1680
cattcaaatt tgagggaatt gcctgtgaaa tcagtaaaca aaaaatttct gaaggattgc    1740
cagccctaga gttccccaat gaaaaataga gctgttggct tctctgagct ccagtggaag    1800
aagaaaacac tagtaccttc agatcctacc cctgaagata atcttagctg ccaagtaaat    1860
agcaacatgc ttcatgaaaa tcctaccaac ctctgaagtc tcttctctct taggtctata    1920
attttttttt aaattttct tccttaaact cctgtgatgt ttccattttt tgttccctaa    1980
tgagaagtca acagtgaaat acgccagaac tgctttatcc cacggaaaat gccaatctct    2040
tctaaaaaaa aacaaaatta aattaaaaac agaatgttgg tttaaaaaac ttcaaagtaa    2100
ttttcaaacg gctttgtatg gttaacatat tctgccaggt ccatgaccac acgtctgtac    2160
catgcaattt aactcttatt tacattgtta tgtttagttt ggttatttgc ttaggtgtgc    2220
atacattcat tcagcaaatg ctgagcacca gccacgtgca cagcagttgc ttttactagt    2280
cttagctcta cgatttaaat ccatgtgtcc aaggggaaa acatattata tttgtaacca    2340
aaaactacta gtttaccaga ggactgaagg gagataaaga ggagttggtt aatgggtaca    2400
aaaatccagt tagatgaaag gaataatata gatagtgttc agtagcagaa tagaatgaac    2460
ataaactatt agtttaaatt atgtgaaatt ccttctattt gatcatattt tacaagaaaa    2520
aacatcaatt ttatatagtc caacttaata cctagcctta tgagttgtat aaggtaaggt    2580
tacctacctg agaagctgat taacattggt tgtacaatct tattcattag agaacatggt    2640
gcttagggtc tgagaccttt tgaaaggtct gagaactctt taaaaaaagg aaa            2693
```

<210> SEQ ID NO 3
<211> LENGTH: 559
<212> TYPE: PRT
<213> ORGANISM: Homo sapiens

<400> SEQUENCE: 3

```
Met Ser Ala Cys Arg Ser Phe Ala Val Ala Ile Cys Ile Leu Glu Ile
1               5                   10                  15

Ser Ile Leu Thr Ala Gln Tyr Thr Thr Ser Tyr Asp Pro Glu Leu Thr
            20                  25                  30

Glu Ser Ser Gly Ser Ala Ser His Ile Asp Cys Arg Met Ser Pro Trp
        35                  40                  45

Ser Glu Trp Ser Gln Cys Asp Pro Cys Leu Arg Gln Met Phe Arg Ser
    50                  55                  60

Arg Ser Ile Glu Val Phe Gly Gln Phe Asn Gly Lys Arg Cys Thr Asp
65                  70                  75                  80

Ala Val Gly Asp Arg Arg Gln Cys Val Pro Thr Glu Pro Cys Glu Asp
                85                  90                  95

Ala Glu Asp Asp Cys Gly Asn Asp Phe Gln Cys Ser Thr Gly Arg Cys
            100                 105                 110

Ile Lys Met Arg Leu Arg Cys Asn Gly Asp Asn Asp Cys Gly Asp Phe
        115                 120                 125

Ser Asp Glu Asp Asp Cys Glu Ser Glu Pro Arg Pro Pro Cys Arg Asp
    130                 135                 140

Arg Val Val Glu Glu Ser Glu Leu Ala Arg Thr Ala Gly Tyr Gly Ile
145                 150                 155                 160

Asn Ile Leu Gly Met Asp Pro Leu Ser Thr Pro Phe Asp Asn Glu Phe
                165                 170                 175

Tyr Asn Gly Leu Cys Asn Arg Asp Arg Asp Gly Asn Thr Leu Thr Tyr
            180                 185                 190

Tyr Arg Arg Pro Trp Asn Val Ala Ser Leu Ile Tyr Glu Thr Lys Gly
        195                 200                 205

Glu Lys Asn Phe Arg Thr Glu His Tyr Glu Glu Gln Ile Glu Ala Phe
    210                 215                 220

Lys Ser Ile Ile Gln Glu Lys Thr Ser Asn Phe Asn Ala Ala Ile Ser
225                 230                 235                 240

Leu Lys Phe Thr Pro Thr Glu Thr Asn Lys Ala Glu Gln Cys Cys Glu
                245                 250                 255

Glu Thr Ala Ser Ser Ile Ser Leu His Gly Lys Gly Ser Phe Arg Phe
            260                 265                 270

Ser Tyr Ser Lys Asn Glu Thr Tyr Gln Leu Phe Leu Ser Tyr Ser Ser
        275                 280                 285

Lys Lys Glu Lys Met Phe Leu His Val Lys Gly Glu Ile His Leu Gly
    290                 295                 300

Arg Phe Val Met Arg Asn Arg Asp Val Val Leu Thr Thr Thr Phe Val
305                 310                 315                 320

Asp Asp Ile Lys Ala Leu Pro Thr Thr Tyr Glu Lys Gly Glu Tyr Phe
                325                 330                 335

Ala Phe Leu Glu Thr Tyr Gly Thr His Tyr Ser Ser Ser Gly Ser Leu
            340                 345                 350

Gly Gly Leu Tyr Glu Leu Ile Tyr Val Leu Asp Lys Ala Ser Met Lys
        355                 360                 365

Arg Lys Gly Val Glu Leu Lys Asp Ile Lys Arg Cys Leu Gly Tyr His
    370                 375                 380

Leu Asp Val Ser Leu Ala Phe Ser Glu Ile Ser Val Gly Ala Glu Phe
385                 390                 395                 400

Asn Lys Asp Asp Cys Val Lys Arg Gly Glu Gly Arg Ala Val Asn Ile
                405                 410                 415
```

-continued

```
Thr Ser Glu Asn Leu Ile Asp Asp Val Val Ser Leu Ile Arg Gly Gly
            420                 425                 430

Thr Arg Lys Tyr Ala Phe Glu Leu Lys Glu Lys Leu Leu Arg Gly Thr
            435                 440                 445

Val Ile Asp Val Thr Asp Phe Val Asn Trp Ala Ser Ser Ile Asn Asp
450                 455                 460

Ala Pro Val Leu Ile Ser Gln Lys Leu Ser Pro Ile Tyr Asn Leu Val
465                 470                 475                 480

Pro Val Lys Met Lys Asn Ala His Leu Lys Lys Gln Asn Leu Glu Arg
                485                 490                 495

Ala Ile Glu Asp Tyr Ile Asn Glu Phe Ser Val Arg Lys Cys His Thr
            500                 505                 510

Cys Gln Asn Gly Gly Thr Val Ile Leu Met Asp Gly Lys Cys Leu Cys
            515                 520                 525

Ala Cys Pro Phe Lys Phe Glu Gly Ile Ala Cys Glu Ile Ser Lys Gln
            530                 535                 540

Lys Ile Ser Glu Gly Leu Pro Ala Leu Glu Phe Pro Asn Glu Lys
545                 550                 555

<210> SEQ ID NO 4
<211> LENGTH: 15
<212> TYPE: PRT
<213> ORGANISM: Homo sapiens

<400> SEQUENCE: 4

Leu Gln Tyr Glu Asn Val Asp Glu Asp Ser Ser Asp Ser Asp Ala
1               5                   10                  15
```